US009070702B2

(12) United States Patent
Gabriel et al.

(10) Patent No.: US 9,070,702 B2
(45) Date of Patent: Jun. 30, 2015

(54) METHOD FOR OBTAINING THREE-DIMENSIONAL ACTIN STRUCTURES AND USES THEREOF

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris Cedex (FR)

(72) Inventors: Jean-Christophe Gabriel, Quaix en Chartreuse (FR); Laurent Blanchoin, Saint Egreve (FR); Manuel Thery, Grenoble (FR); Remi Galland, Grenoble (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris Cedex (FR)

( * ) Notice: Subject to any disclaimer, the term of this patent is extended or adjusted under 35 U.S.C. 154(b) by 0 days.

(21) Appl. No.: 14/377,263

(22) PCT Filed: Feb. 7, 2013

(86) PCT No.: PCT/EP2013/052393
§ 371 (c)(1),
(2) Date: Aug. 7, 2014

(87) PCT Pub. No.: WO2013/117624
PCT Pub. Date: Aug. 15, 2013

(65) Prior Publication Data
US 2015/0048513 A1 Feb. 19, 2015

(30) Foreign Application Priority Data

Feb. 10, 2012 (EP) .................................... 12305148

(51) Int. Cl.
*H01L 23/48* (2006.01)
*H01L 23/00* (2006.01)
(Continued)

(52) U.S. Cl.
CPC ................. *H01L 24/64* (2013.01); *B82Y 15/00* (2013.01); *C07K 14/4716* (2013.01); *B82Y 5/00* (2013.01);
(Continued)

(58) Field of Classification Search
CPC ......... H01L 23/00; B29C 41/00; C07K 14/47
USPC ..................... 257/773; 530/350; 264/104, 293
See application file for complete search history.

(56) References Cited

U.S. PATENT DOCUMENTS 5,976,819 A * 11/1999 Finkel et al. ................. 435/7.24
7,981,774 B2 * 7/2011 Grier et al. ..................... 438/479
(Continued)

FOREIGN PATENT DOCUMENTS

DE 10 2007 022 915 11/2008
WO WO 2004/036011 4/2004
WO WO 2012/020011 2/2012

OTHER PUBLICATIONS

Yi, J. et al. "Engineering an artificial amoeba propelled by nanoparticle-triggered actin polymerization" *Nanotechnology*, 2009, pp. 1-8, vol. 20, No. 8.
(Continued)

*Primary Examiner* — Caleb Henry
(74) *Attorney, Agent, or Firm* — Saliwanchik, Lloyd & Eisenschenk

(57) ABSTRACT

The present invention relates to a method for preparing three-dimensional actin structures having a well-defined shape and displaying improved mechanical rigidity. This method comprises the steps of (a) providing a polymerization solution comprising actin monomers, a branching agent and a capping agent, (b) providing at least one surface having thereon a pattern which is coated with a nucleating agent, and (c) contacting the at least one surface of step (b) with the polymerization solution of step (a) so as to induce the polymerization of actin and obtain the said desired three-dimensional actin structure. Applications of the present invention in various technological fields such as microelectronics are also provided.

17 Claims, 10 Drawing Sheets

(51) Int. Cl.
*C07K 14/47* (2006.01)
*B82Y 5/00* (2011.01)
*B82Y 40/00* (2011.01)
*B82B 3/00* (2006.01)
*H01L 25/065* (2006.01)
*H01L 25/00* (2006.01)
*B29C 41/00* (2006.01)
*B82Y 15/00* (2011.01)

(52) U.S. Cl.
CPC .............. *B82Y 40/00* (2013.01); *B82B 3/0052* (2013.01); *B82B 3/0019* (2013.01); *H01L 25/0652* (2013.01); *H01L 25/0657* (2013.01); *H01L 2225/06517* (2013.01); *H01L 2225/06513* (2013.01); *H01L 2225/06524* (2013.01); *H01L 2224/16105* (2013.01); *H01L 2224/16137* (2013.01); *H01L 2224/13693* (2013.01); *H01L 2224/16106* (2013.01); *H01L 2224/16059* (2013.01); *H01L 2224/1366* (2013.01); *H01L 24/11* (2013.01); *H01L 24/13* (2013.01); *H01L 24/16* (2013.01); *H01L 2224/13018* (2013.01); *H01L 2224/13193* (2013.01); *H01L 2224/13639* (2013.01); *H01L 2224/13644* (2013.01); *H01L 2224/13647* (2013.01); *H01L 2224/16145* (2013.01); *H01L 2224/1613* (2013.01); *H01L 25/50* (2013.01); *H01L 2924/1461* (2013.01); *B29C 41/003* (2013.01); *H01L 24/70* (2013.01); *H01L 2924/0695* (2013.01)

(56) References Cited

U.S. PATENT DOCUMENTS

| | | | |
|---|---|---|---|
| 8,022,417 B2* | 9/2011 | Takiar et al. | 257/84 |
| 2002/0050611 A1* | 5/2002 | Yitzchaik et al. | 257/315 |
| 2003/0013208 A1* | 1/2003 | Jendoubi | 436/518 |
| 2003/0170726 A1 | 9/2003 | Fradelizi et al. | |
| 2004/0110347 A1* | 6/2004 | Yamashita | 438/286 |
| 2005/0106629 A1 | 5/2005 | McGrath et al. | |
| 2006/0003399 A1 | 1/2006 | Tomasevic et al. | |
| 2007/0059727 A1* | 3/2007 | Deymier et al. | 435/6 |
| 2010/0009338 A1* | 1/2010 | Zhang et al. | 435/5 |
| 2013/0130394 A1* | 5/2013 | Thery et al. | 436/86 |
| 2014/0073063 A1* | 3/2014 | Lieber et al. | 438/1 |
| 2014/0288192 A1* | 9/2014 | Vitaliano et al. | 514/773 |
| 2014/0363422 A1* | 12/2014 | Hayday et al. | 424/131.1 |

OTHER PUBLICATIONS

Database Biosis [Online] Accession No. PREV200400126365, Fisher, C. et al. "Micropatterning of ActA to study actin-based motility" Jan. 2004, p. 1, vol. 86, No. 1.

Nakamura, H. et al. "Shape Control of Filamentous Motor Proteins for Bio-Nano Driving Units" *IEEE 20th International Conference on Micro Electro Mechanical Systems*, Jan. 21-25, 2007, pp. 409-412, XP031203731.

Wong, T. et al. "Manufacture of Nanoscale Structures through Integrated Top-down and Bottom-up Approaches" *Proceedings of the 7th IEEE International Conference on Nanotechnology*, Aug. 2-5, 2007, XP031307738, pp. 126-130.

Yi, J. et al. "Microsphere Dynamics for Actin Based Nanorobotic Motility" *Nanotechnology*, Aug. 12, 2003, pp. 725-728, vol. 2.

Roos, W. et al. "Freely Suspended Actin Cortex Models on Arrays of Microfabricated Pillars" *Chemphyschem*, 2003, pp. 872-877, vol. 4.

Michelot, A. et al. "Actin-Filament Stochastic Dynamics Mediated by ADF/Cofilin" *Current Biology*, May 15, 2007, pp. 825-833, vol. 17.

Uhrig, K. et al. "Optical force sensor array in a microfluidic device based on holographic optical tweezers" *Lab on a Chip*, 2009, pp. 661-668, vol. 9.

Written Opinion in International Application No. PCT/EP2011/063676, Oct. 10, 2011, pp. 1-8.

Xu, X.-P. et al. "Three-dimensional recontructions of Arp2/3 complex with bound nucleation promoting factors" *The EMBO Journal*, 2012, pp. 236-247, vol. 31, No. 1.

Ti, S.-C. et al. "Structural and biochemical characterization of two binding sites for nucleation-promoting factor WASp-VCA on Arp2/3 complex" *PNAS*, Aug. 16, 2011, pp. E463-E471, vol. 108, No. 33.

Blanchoin, L. et al. "Interactions of ADF/cofilin, Arp2/3 complex, capping protein and profilin in remodeling of branched actin filament networks" *Current Biology*, Oct. 14, 2000, pp. 1273-1282, vol. 10, No. 20.

Achard, V. et al. "A 'Primer'-Based Mechanism Underlies Branched Actin Filament Network Formation and Motility" *Current Biology*, Mar. 9, 2010, pp. 423-428, vol. 20, No. 5.

Akin, O. et al. "Capping Protein Increases the Rate of Actin-Based Motility by Promoting Filament Nucleation by the Arp2/3 Complex" *Cell*, May 30, 2008, pp. 841-851, vol. 133, No. 5.

Chen, Z. et al. "Structure and control of the actin regulatory *Wave* complex" *Nature*, Nov. 25, 2010, pp. 533-538, vol. 468, No. 7323.

Ferron, F. et al. "Structural basis for the recruitment of profilin-actin complexes during filament elongation by Ena/VASP" *The EMBO Journal*, Oct. 1, 2007, pp. 4597-4606, vol. 26, No. 21.

Yao, L. et al. "Fabrication of semiconductor nanowires by conjugation of quantum dots to actin filaments" *Anal Bioanal Chem*, Sep. 3, 2009, pp. 1563-1566, vol. 395, No. 5.

Patolsky, F. et al. "Actin-based metallic nanowires as bio-nanotransporters" *Nature Materials*, Oct. 1, 2004, pp. 692-695, vol. 3, No. 10.

Campellone, K. G. et al. "A nucleator arms race: cellular control of actin assembly" *Nature Reviews, Molecular Cell Biology*, Apr. 1, 2010, pp. 237-251, vol. 11, No. 4.

Sundberg, M. et al. "Actin Filament Guidance on a Chip: Toward High-Throughput Assays and Lab-on-a-Chip Applications" *Langmuir*, Aug. 1, 2006, pp. 7286-7295, vol. 22, No. 17.

Galland, R. et al. "Fabrication of three-dimensional electrical connections by means of directed actin self-organization" *Nature Materials*, Feb. 10, 2013, pp. 416-421, vol. 12, No. 5.

Written Opinion in International Application No. PCT/EP2013/052393, Jun. 12, 2013, pp. 1-8.

\* cited by examiner

Connections made by actin structure of the "column-type"

Connexion of 2 chips on the same wafer by interacting together two structures having T-shape

SEQUENCE LISTING

<160> NUMBER OF SEQ ID NOS: 1

<210> SEQ ID NO 1
<211> LENGTH: 388
<212> TYPE: PRT
<213> ORGANISM: Homo sapiens

<400> SEQUENCE: 1

```
Lys Arg Lys Glu Lys Arg Lys Gln Lys Gln Lys Asn Leu Asp Arg Pro
1               5                   10                  15

His Glu Pro Glu Lys Val Pro Arg Ala Pro His Asp Arg Arg Arg Glu
            20                  25                  30

Trp Gln Lys Leu Ala Gln Gly Pro Glu Leu Ala Glu Asp Asp Ala Asn
        35                  40                  45

Leu Leu His Lys His Ile Glu Val Ala Asn Gly Pro Ala Ser His Phe
    50                  55                  60

Glu Thr Arg Pro Gln Thr Tyr Val Asp His Met Asp Gly Ser Tyr Ser
65                  70                  75                  80

Leu Ser Ala Leu Pro Phe Ser Gln Met Ser Glu Leu Leu Thr Arg Ala
                85                  90                  95

Glu Glu Arg Val Leu Val Arg Pro His Glu Pro Pro Pro Pro Pro
            100                 105                 110

Met His Gly Ala Gly Asp Ala Lys Pro Ile Pro Thr Cys Ile Ser Ser
```

-continued

```
            115                 120                 125
Ala Thr Gly Leu Ile Glu Asn Arg Pro Gln Ser Pro Ala Thr Gly Arg
            130                 135                 140

Thr Pro Val Phe Val Ser Pro Thr Pro Pro Pro Pro Pro Pro Pro Leu
145                     150                 155                 160

Pro Ser Ala Leu Ser Thr Ser Ser Leu Arg Ala Ser Met Thr Ser Thr
                    165                 170                 175

Pro Pro Pro Pro Val Pro Pro Pro Pro Pro Pro Ala Thr Ala Leu
                180                 185                 190

Gln Ala Pro Ala Val Pro Pro Pro Ala Pro Leu Gln Ile Ala Pro
            195                 200                 205

Gly Val Leu His Pro Ala Pro Pro Ile Ala Pro Pro Leu Val Gln
            210                 215                 220

Pro Ser Pro Pro Val Ala Arg Ala Ala Pro Val Cys Glu Thr Val Pro
225                     230                 235                 240

Val His Pro Leu Pro Gln Gly Glu Val Gln Gly Leu Pro Pro Pro Pro
                    245                 250                 255

Pro Pro Pro Pro Leu Pro Pro Pro Gly Ile Arg Pro Ser Ser Pro Val
                260                 265                 270

Thr Val Thr Ala Leu Ala His Pro Pro Ser Gly Leu His Pro Thr Pro
            275                 280                 285

Ser Thr Ala Pro Gly Pro His Val Pro Leu Met Pro Pro Ser Pro Pro
            290                 295                 300

Ser Gln Val Ile Pro Ala Ser Glu Pro Lys Arg His Pro Ser Thr Leu
305                     310                 315                 320

Pro Val Ile Ser Asp Ala Arg Ser Val Leu Leu Glu Ala Ile Arg Lys
                    325                 330                 335

Gly Ile Gln Leu Arg Lys Val Glu Glu Gln Arg Glu Gln Glu Ala Lys
                340                 345                 350

His Glu Arg Ile Glu Asn Asp Val Ala Thr Ile Leu Ser Arg Arg Ile
            355                 360                 365

Ala Val Glu Tyr Ser Asp Ser Glu Asp Ser Glu Phe Asp Glu Val
            370                 375                 380

Asp Trp Leu Glu
385
```

METHOD FOR OBTAINING THREE-DIMENSIONAL ACTIN STRUCTURES AND USES THEREOF

CROSS-REFERENCE TO RELATED APPLICATION

This application is the U.S. national stage application of International Patent Application No. PCT/EP2013/052393, filed Feb. 7, 2013.

FIELD OF THE INVENTION

The present invention relates to a method for preparing oriented three-dimensional actin structures of the nano- or micrometer scale, and uses thereof, in particular, in the fields of microelectronics.

BACKGROUND OF THE INVENTION

The development of new methods for preparing three-dimensional structures of the nano- or the micrometer scale is of great interest in various technological fields such as biotechnology, microelectronics, microfluidics and biomaterials.

In microelectronics, research have focused on the development of new approaches for miniaturizing classical 2D integrated circuits into smaller 3D-structures in which interconnected silicon wafers (3D-IC (3D-integrated circuits)) or chips (3D-packaging) are stacked. The so-called "3D-technology" enables to provide greater functionality and higher component density while decreasing the form factor. One of the biggest challenges of 3D-technologies remains the creation of vertical electrical connections between stacked chips or stacked silicon wafers using nano- or microstructures such as nanowires. Nowadays, microelectronic devices are mainly available by conventional top-down processes such as photolithography. But, for the foreseeable future, such technologies are believed to remain inappropriate for the large-scale production of microelectronic devices.

Nanotechnology research thus put a great emphasis on the "Bottom-Up" strategies. These strategies are based on the self-assembly of molecular building blocks for creating three dimensional nano- or microstructures to be integrated in larger and functional microdevices. Appropriate molecular building blocks encompass inorganic compounds able to form crystals as well as biological molecules such as DNA, peptides and proteins. In that respect, proteins are very attractive building blocks because of their physical sizes, their highly specific interactions, their high degree of organization and their ability to be chemically functionalized or coated.

Several publications describe nanowires obtained from protein fibres.

Scheibel et al. (PNAS, 2003, 1000, 4527-4532) describe the use of self-assembling amyloid fibres from *Saccharomyces cerevisiae* prion determinant to construct nanowire elements. The said nanowire elements were subsequently metallized with silver or gold so as to produce conductive metal wires of 100 nm wide.

Patolsky et al. (Nature Materials, 2004, 4, 692-695) describe gold wires (1-4 µm long and 80-200 nm high) exhibiting high electrical conductivity which are obtained by polymerization of G-actin labelled with Au (gold) nanoparticles followed by the catalytic enlargement by metallization process. In the same way, Yao et al. (Analytical and Bioanalytical Chemistry, 395, 1563-1566) describe semiconductor nanowires obtained by conjugation of quantum dots to actin filaments.

However, few studies relate to methods for actually preparing three-dimensional protein structures more complex than nanowires.

Nakamura et al. (MEMS proceedings, 2007, Japan) describe that, when G-actin and fascin solution was confined and polymerized in Polydimethylsiloxane (PDMS) micro chambers, the shape of the actin bundles may follow the geometry of the chambers. It clearly appears that such a method is quite limited and only enables to obtain very few flat actin structures.

Brough et al. (Soft Mater, 2007, 3, 541-546) has proposed a method for preparing three-dimensional actin structures with nano-resolution patterns in the XY direction and on the micron pattern on Z direction while controlling the precise location of said structures on substrates such as silicon wafers. This method is based on the use of streptavidin nanopatterns for immobilizing biotinylated gelsolin-F-actin complex and subsequently promoting the polymerization of actin filaments. Gelsolin is indeed a capping agent which binds the barbed of actin filament. Consequently, the polymerization of actin filaments only occurred from pointed ends and is thus very slow. The resulting polymerized actin filaments are unbranched and display a length of at most 3-4 µm. Even if the actin filaments grew in out-of-plane direction from the nanopatterns, no well-orientated and well-defined three-dimensional actin structure could be actually observed.

Huang et al. (Langmuir 2006, 22, 8635-8638) describes a method similar to that of Brough et al. This method is based on the immobilization of pre-formed actin filaments on patterns. The immobilized actin filaments are then aligned along a desired direction using an electric field.

US 2005/0106629 reports a method for preparing a three-dimensional actin column based on the use of a first surface (nucleating plate) patterned with nucleating agent and a second surface (binding plate) patterned with capture agent. As explained in Example 3 of this document, the two patterned surfaces are brought into contact and aligned within a small fluid chamber under an inverted microscope. The fluid chamber is filled with a polymerization mixture to initiate column growth from nucleating plate. For enabling the growth of the actin column, the binding plate is moved away from the nucleating plate at a rate approximately equal to the rate of the column growth but not faster. In other words, the column grows as a bundle of parallel actin filaments, each actin filament being in contact by its first end to a nucleating agent on the nucleating plate and being connected by its second end to a capture agent on the binding plate. Even if said method virtually enables to control the location of the three-dimensional structures of actin, it clearly appears that such a method is very difficult to implement in mass production process since the distance of the two surfaces must be increased with a very precise rate, during the polymerization process, in order to promote the unidirectional growth of actin filaments. Moreover, since US 2005/0106629 does not provide any experimental result, the experimental feasibility of this method remains to be demonstrated.

There is thus a need for novel methods enabling the preparation of three-dimensional structures of actin on the nano- or micrometer scale while controlling precisely the shape, the orientation and the spatial location of said structures.

SUMMARY OF THE INVENTION

The invention relates to a method for preparing a three dimensional structure of actin, said method comprising the steps of:

a. Providing a polymerization solution comprising actin monomers, an Arp2/3 complex, a capping agent, ATP, a divalent cation and profilin wherein the molar ratio of Arp2/3 to capping agent preferably ranges from 0.1 and 4.0, b. Providing at least one surface having thereon at least one pattern, the said pattern being coated with a nucleating agent selected from the group consisting of members of the WASp family, members from SCAR/WAVE family, VCA domains thereof, peptides from VCA domains such as WA and pWA, functional homologs of SCAR/WAVE and WASp proteins such as ActA from *Listeria* and RickA from *Rickettsia*, and combinations thereof, and c. Contacting the at least one surface of step (b) with the polymerization solution of step (a) so as to induce the polymerization of actin and obtain the said three-dimensional actin structure.

In some embodiments, the said method is characterized by the fact that:

in step b), a first surface and a second surface are provided, wherein each surface has thereon a pattern coated with a nucleating agent and the said first and second surfaces are positioned so that:

the said surfaces are substantially parallel to each other and separated by a distance of at most 1 mm, and the pattern of the first surface and that of the second surface are face-to-face so that their centers are substantially aligned; and in step c), the two patterned surfaces of step b) are contacted with the polymerization solution of step a) so as to induce the polymerization of a tridimensional actin substructure from each said pattern, thereby the final three-dimensional actin structure results from the interaction of the said two actin substructures which have grown face-to-face.

In some other embodiments, the polymerization solution of step a) is characterized by one or several of the following features: (i) the molar ratio of actin monomers to the Arp2/3 complex may range from 5 to 500, preferably from 5 to 100, (ii) the concentration of actin monomers may range from 0.01 µM to 100 µM, preferably from 0.1 µM to 10 µM, and (iii) the molar ratio of profilin to actin monomers ranges from to 1 to 10, preferably from 2 to 5.

The polymerization solution of step a) may further comprise a cross-linking protein preferably selected from α-actinin, fascin and combinations thereof. The molar ratio of the said cross-linking protein to Arp2/3 complex may range from 0.1 to 5. The polymerization solution may also contain phalloidin.

In some further embodiments, in the polymerization solution of step a), the molar ratio of actin monomers to the Arp2/3 complex ranges from 5 to 20 or from 20 to 50.

In the embodiment wherein two patterned surfaces are provided, the first surface and the second surface may have thereon a plurality of patterns so that the center of each pattern on the first surface is substantially aligned with that of a pattern on the second surface. Moreover, the pattern on the first surface may have a shape complementary to that of the pattern on the second surface. Alternatively, the pattern on the first surface may have the same shape as the pattern on the second surface. Furthermore, the ratio of (i) the distance between the first and the second surfaces to (ii) the width of the largest pattern may be at most 10. On the other hand, the largest dimension (i.e the dimension along the longitudinal axis) of the pattern(s) used in the methods according to the invention is at most 300 µm.

In some embodiments, the patterned surface(s) provided in step b) is/are essentially planar or planar.

In some further embodiments the method according to the invention comprises one or several of the following steps:

A step of removing the polymerization solution once the three-dimensional actin structure has been obtained, A step of incubating the three-dimensional actin structure obtained in step c) with a solution comprising a cross-linking protein, A step of incubating the three-dimensional actin structure obtained in step c) with a solution comprising a chemical cross-linker, a chemical fixative agent and/or an agent able to inhibit actin depolymerization, A step of chemically functionalizing the three-dimensional actin structure obtained in step c), and/or A step of metallization of the three-dimensional actin structure obtained in step c).

Another object of the invention is a three-dimensional actin structure obtainable by the method according to the invention. The three-dimensional actin structure is preferably composed of a branched network of actin, the distance between two consecutive actin branch points being at most 1 µm.

The invention also relates to a planar surface comprising thereon at least one actin three-dimensional structure obtainable by the method according to the invention. A further object of the invention is a device comprising two surfaces substantially parallel to each other wherein the said surfaces are connected to each other by at least one three-dimensional actin structure obtainable by the method according to the invention.

A further object of the invention is a process for creating a conductive connection between two surfaces comprising the steps of:

i. Preparing a three dimensional actin structure actin by the method as defined herein, ii. Coating the three-dimensional structure of actin obtained in step i) with a conductive or semi-conductive layer, and iii. Optionally, removing the backbone of actin.

In some embodiments, step (ii) of the process comprises submitting the three-dimensional actin structure obtained in step i) to a metallization process so as to coat the said three dimensional structure of actin with a conductive metallic layer.

The two surfaces may be selected from chips and silicon wafers and a plurality of conductive connections may be created between the said two surfaces during the said process.

Accordingly, the invention also relates to an electronic device comprising two surfaces which are connected together by at least one conductive connection wherein the said at least on conductive connection is obtained by the process as defined here above. Preferably, the said two surfaces are selected from chips and silicon wafers.

BRIEF DESCRIPTION OF THE DRAWINGS

FIGS. 2 (a) and (b): 3D representation of actin structures polymerized without Capping Protein from empty circle shaped pattern (3D reconstruction of confocal acquisition). FIGS. 2 (c) and (d): 3D representation of oriented structures polymerized with Capping Protein from empty and full circle shaped patterns respectively (3D reconstruction of confocal acquisition). The actin structures were labeled with Alexa-548 fluorophores to visualize them with optical microscopy.

FIG. 3 (a) shows the principle of the formation of said structures. FIG. 3 (b) shows confocal acquisition of a 3D connection. Figure (c) shows the 3D reconstruction of a single 3D structure. FIG. 3 (d) shows the 3D reconstruction of a plurality 3D structures (obtained simultaneously) acquired through a confocal microscope. The actin structures were labeled with Alexa-548 fluorophores to visualize them with optical microscopy. These structures were obtained as described in Example 1.

FIG. 4(a) shows the principle of the formation of said structure. FIG. 4(b) shows the confocal acquisition of a direct 3D connection. FIG. 4(c) shows 3D reconstruction of a 3D structure acquired through a confocal microscope. The actin structures were labeled with Alexa-548 fluorophores to visualize them with optical microscopy. This structure was obtained as described in Example 2.

FIG. 5(a) shows the principle of the formation of said structure. FIG. 5(b) shows the confocal acquisition of a direct 3D connection. FIG. 5(c) shows 3D reconstruction of 3D structure acquired through a confocal microscope. The actin structures were labeled with Alexa-548 fluorophores to visualize them with optical microscopy. This structure was obtained as described in Example 3.

DEFINITIONS

Figure 1:
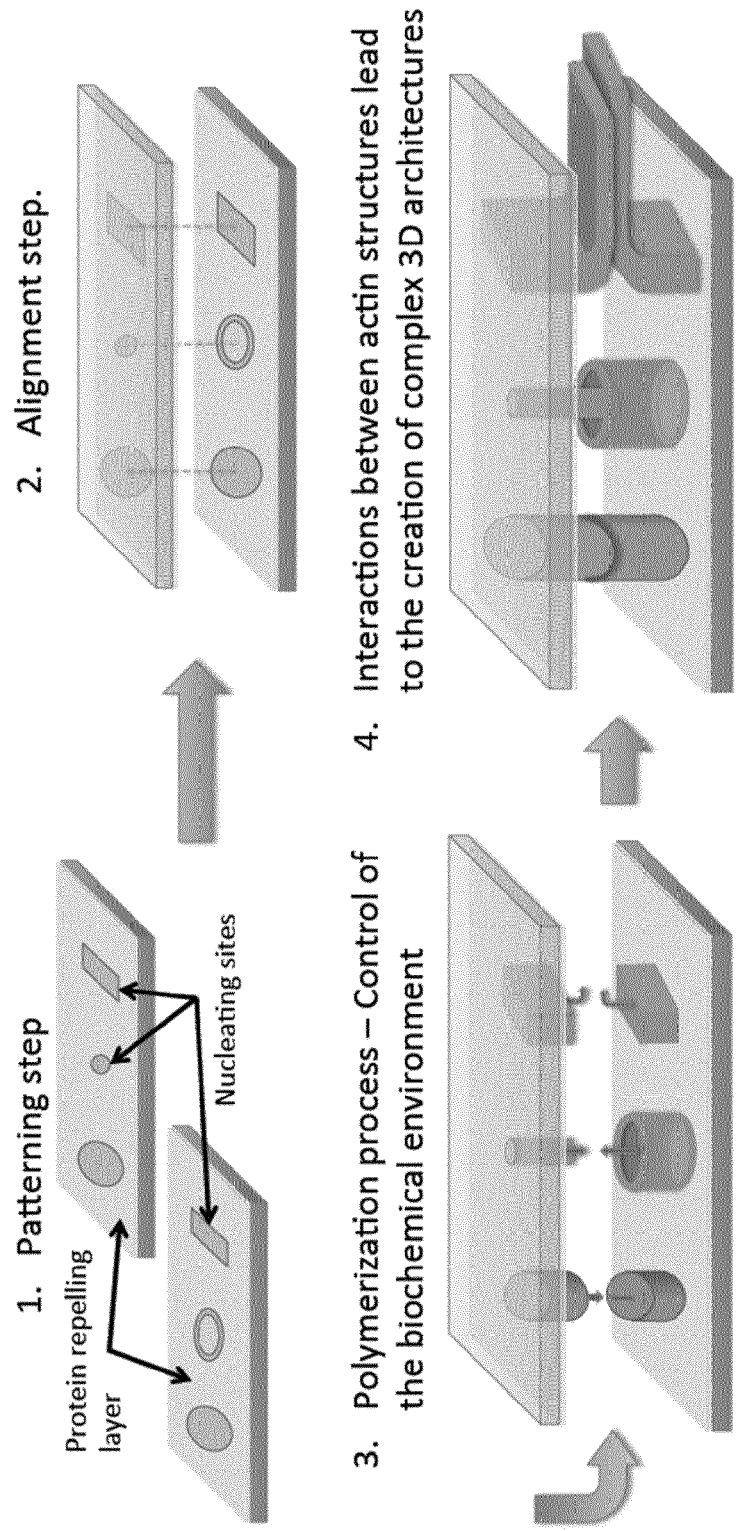
FIG. 1 shows an embodiment of the method according to the invention wherein a three-dimensional actin structure is obtained by interacting together two actin substructures which have grown face-to-face. In step 1, three appropriate patterns are prepared on each surface. The said surfaces comprise thereon a layer preventing the non-specific binding of proteins (protein repelling layer). Nucleating agents are immobilized on patterns so as to form nucleation site for actin polymerization. In step 2, the two patterned surfaces are aligned face-to-face so as to create a reaction chamber. Each pattern of the first surface is vertically aligned with a pattern on the second surface. In step 3, the space between the two surfaces (i.e. the reaction chamber) is filled with the polymerization solution according to the invention. The said solution enables to fully control the biochemical environment and induce actin polymerization simultaneously from each pattern. From each pattern, a three-dimensional actin substructure grows perpendicularly to the surface while keeping the shape of the pattern. In step 4, the desired three-dimensional actin structures result from the interaction of two actin substructures which have grown face-to-face. The figure shows three types of final actin structures, namely: a structure having the shape of a column (right), a structure of the "receptacle-plug" type (middle) and a structure having a "T-shape" (left).

"Actin" encompasses actin filaments as well as actin monomers. As used herein, Actin filaments results from the association of at least two monomers of actin. Actin monomer is also called in the art "G-actin" or globular actin whereas actin filament is also called "F-actin" or filamentous actin. Actin filament has two ends: the first end is called the "barbed end" and the second end is called the "pointed end". Actin filament has a structural polarity: the barbed end is the (+) end and the pointed end is the (−) end.

Actin monomer encompasses naturally-occurring actin monomers as well as variants, homologs and fragments thereof. Actin monomers which may be used for implementing the present invention may derive from any source. For example, appropriate G-actin may be an alpha, beta or gamma actin isoform found in vertebrates.

As used herein, a "three-dimensional actin structure" refers to a branched network of short actin filaments.

As used herein, by "Branching agent" is meant a protein or a protein complex able to promote the initiation of new actin assembly that branches off an existing filament. In other words, a "Branching agent" initiates the formation of a new filament (also called daughter filament) onto a pre-existing actin filament (also called mother actin filament) after being activated by a nucleating agent. An example of "branching agent" is Arp2/3 complex which promotes actin polymerization on the barbed end. In the context of the present invention, one may use an Arp2/3 complex from any source such as yeasts, insects and vertebrates. The Arp2/3 complex encompasses naturally-occurring Arp2/3 complex (i.e. wild-type Arp2/3 complex) as well as variants, homologs and fragments thereof. The branching agent may be recombinant. For review concerning Arp2/3 complex, see Goley and Welch, Nature Reviews, 2006, 7, 713-726.

As used herein, by "capping agent" or "capping protein" is meant a protein or a protein complex able to bind in vitro the barbed end of actin filament, thereby preventing the addition or the loss of actin subunits from the said end. In other words, a capping agent is able to interrupt actin polymerization on the barbed end of an actin filament and thus block its growth while preventing its depolymerization. Capping agents encompass, without being limited to, Capping proteins (also called CP), gelsolin, cytochalasin D, Eps8, variants, homologs and fragments thereof. Other examples of capping agents are Abp1 and Aim3 and ADF/cofilin in combination with Aip1 or variants and homologs thereof. In addition FH2 domain of formins or variants may be also used as capping agents.

Preferably, the capping agent according to the invention may further have a dissociation constant (Kd) for the barbed end of actin filament lower than 1 µM, preferably lower than 100 nM and even lower than 10 nM. The Kd of the capping agent for the barbed end of F-actin may be determined as taught by Huang et al., Journal of Biological Chemistry, 2003, 278, 44832-44842. Briefly, Kd value may be determined by measuring the rate of elongation at the barbed end of actin filament. For example, the effect of capping agent on the rate of elongation may be determined by incubation of 0.4 µM of preformed actin filament (e.g. from for rabbit muscle actin) with increasing concentration of capping agent before addition of 1 µM actin (5% pyrene-labeled) and 3 excess of profilin over actin at room temperature. The initial rate of elongation may be plotted versus the concentration of the capping agent concentration. The Kd for capping agent binding to the barbed end of actin filament was determined as the amount of capping protein that decreases the initial rate of elongation by 50% (for illustration see FIG. 6 of the Huang et al. supra).

In the context of the present invention, the capping agent is preferably selected from the group of Capping proteins (CP), variants, homologs and fragments thereof. Capping protein, which is also known as β-actinin, CapZ in skeletal muscle and Cap32/34 in *Dictyostelium*, is a αβ heterodimer. CP is highly conserved in eukaryotic cells. Highly conserved homologs of CP are found in nearly all eukaryotic cells, including fungi, higher plants and various cells and tissues in vertebrates. CP from any source may be used for implementing the present invention. In some embodiments, CP from a mammal is used. CP may be a recombinant CP.

For review concerning Capping Protein see Shafer and Cooper, Annual Review of Cell and developmental Biology, 1995, 11, 497-518, the disclosure of which being incorporated herein by reference.

By "nucleating agent" or "nucleation agent" is meant a protein or a fragment thereof able to activate the branching agent so as to initiate actin polymerization. The actin nucleation agent is also called in the art "Nucleation Promoting Factor" (NPF). The actin nucleation agent encompasses, without being limited to, ActA (Actin assembly-inducing protein), IscA, RickA, WASp (Wiskott-Aldrich Syndrome Protein), N-WASP, SCAR (Suppressor of cyclic AMP repressor), a VCA domain (Verprolin-homology, Cofilin-homology, Acidic regions) or WA region, as pWA peptides. The actin nucleation agent also includes analogues (chimeric forms or mutants) and fragments thereof capable of initiating actin polymerization. The actin nucleation agents are disclosed in US 2006/0003399 and US2005/0106629, the disclosure thereof being incorporated herein by reference. Other suitable actin nucleation agents are also disclosed in the following references: Pollard et al., 2000, Annu Rev Biophys Biomol Struct.; 29, 545-76; Higgs and Pollard, 2001, Annu Rev Biochem. 70, 649-76.

As used herein, the "molar ratio of a first molecule to a second molecule" is the quotient obtained by dividing the concentration of the first molecule by the concentration of the second molecule.

As used herein, a "variant" or a "mutant" of a first protein refers to a protein having an amino acid sequence which differs from that of the said first protein in virtue of one or several amino acid modifications. Amino acid modifications encompass amino acid deletion, amino acid insertion and amino acid substitution. The amino acid sequence of a "variant" or a "mutant" of a wild-type protein has generally at least 70%, preferably at least 80% and more preferably at least 90% identity with the amino acid sequence of said wild-type protein.

As used herein, by "at least one" is meant one or several. Accordingly "providing at least one patterned surface" means that "one patterned surface" or "several patterned surfaces" is/are provided.

As used herein, by "cross-linking protein" is meant a protein able to link together two actin filaments. Various proteins are known to cross-link actin filaments together. For instance, the actin cross-linking proteins may be alpha-actinin, fascin, EF-1, Scruin, villin, dematin, fimbrin, spectrin, dystrophin, ABP 120, filamin, fragments or variants thereof. In the context of the present invention, preferred cross-linking proteins are fascin, alpha-actinin, fragments, variants and combinations thereof.

DETAILED DESCRIPTION OF THE INVENTION

The Applicant conceived a method for preparing three-dimensional actin structures having a defined orientation and shape on a precise location.

As fully-described in the prior art, the polymerization of actin in solution leads to random and twisted actin networks without control on their shape and their mechanical behaviors. The Applicant tried to fix this problem by controlling precisely the location of the nucleation site by immobilizing nucleating agents onto a surface by patterning technology. Such a strategy was indeed inefficient to obtain a defined and self-oriented tridimensional structure as illustrated in FIGS. 2a and 2b.

Surprisingly, the Applicant showed that the presence of a capping agent together with that of Arp2/3 complex during the actin polymerization process actually enables to obtain a well-oriented, dense and well-defined actin three-dimensional structure. Indeed, when contacting the patterned surface with a polymerization solution comprising a branching agent such as Arp2/3 complex, actin monomers and a capping agent, the polymerization of actin filaments only occurred from the nucleation sites of the pattern. Surprisingly, an actin network grew perpendicularly to the said surface while keeping the shape of the pattern. Noteworthy, the final actin structure is self-oriented and thus there is no need of an external mean such as electric or magnetic field for properly orientating it along a desired direction.

Figure 2:
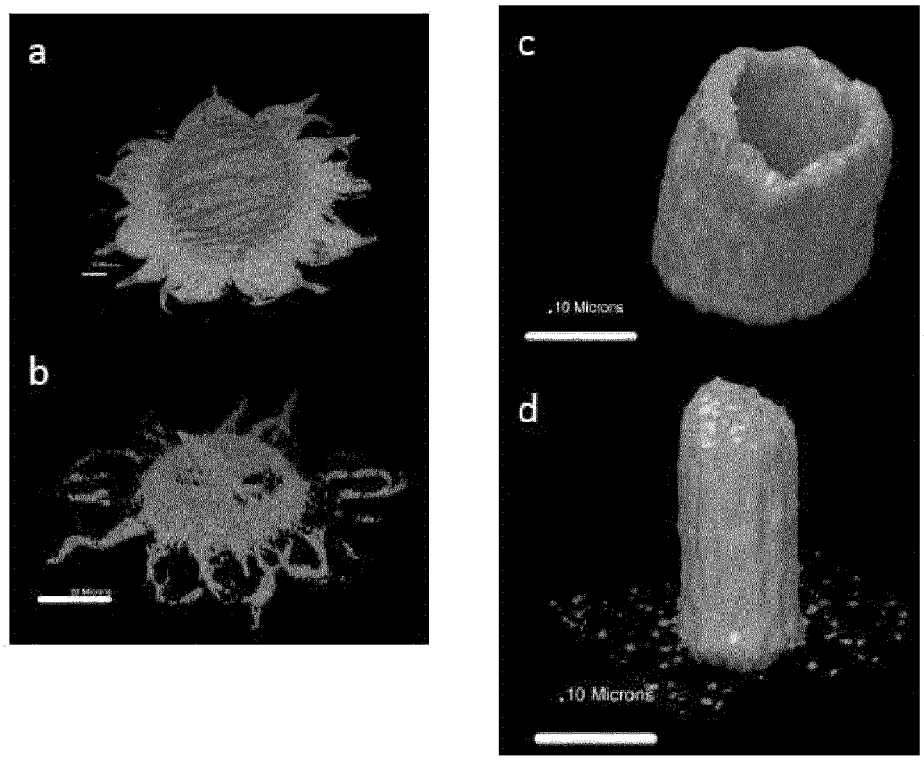
FIG. 2 shows the effect of capping protein on the formation of three-dimensional actin structure in an Arp2/3 polymerization pathway. The presence of capping protein leads to the formation of an oriented structure that grows perpendicularly to the substrate and that conserves the shape of the pattern all along its growth.
Figure 9A:
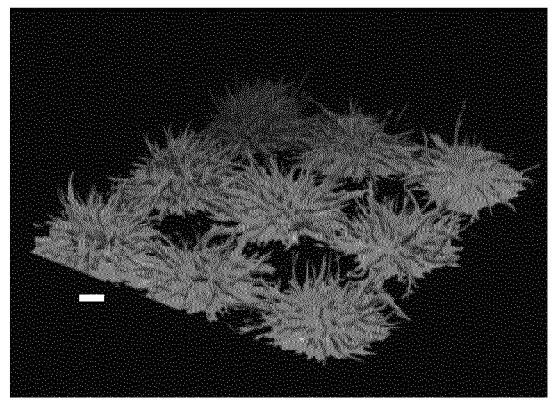
FIG. 9A shows the 3D reconstruction of confocal images of an actin network architecture obtained from an array of 9 torus-shaped micro-patterns in the absence of capping proteins.
Figure 9B:
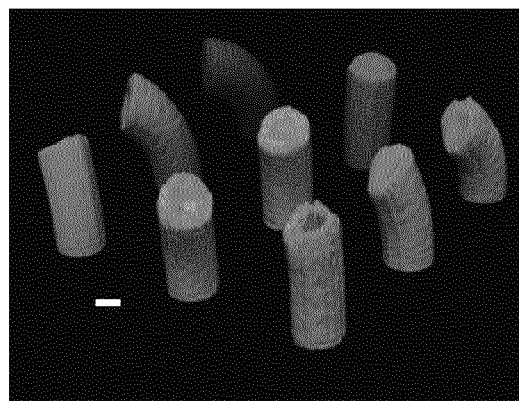
FIG. 9B shows the 3D reconstruction of confocal images of an actin network architecture obtained from an array of 9 torus-shaped micro-patterns in the presence of capping proteins (see example 5). Scale bars represent 10 µm.

The effects of the capping agent on the general structure of the final actin network are clearly shown in FIG. 2. In the presence of a capping agent, a well-structured empty actin cylinder of more than 20 µm of height was obtained from an empty 10 µm-diameter round pattern (see FIG. 2c) whereas, in the absence of capping agent, the actin filaments grew out of plane but without a defined direction, which led to an unfolded actin structure with no internal cohesion and no significant mechanical rigidity (see FIGS. 2a and 2b and also FIGS. 9A and 9B).

The three-dimensional actin structure obtained in the presence of the capping agent consists in a dense and highly branched network of short actin filaments displaying mechanical rigidity. Without to be bound by any theory, the Applicant believes that both the presence of the capping agent and the Arp2/3 complex play a crucial role in the internal structure and the mechanical properties of the final actin three-dimensional object.

The Applicant also showed that the method according to the invention may be very useful for creating a large variety of three-dimensional actin structures, which may result from the interaction of two three-dimensional actin substructures which have grown face-to-face The Applicant showed that in the presence of the polymerization mixture according to the invention, two three-dimensional actin substructures, which had grown face-to-face from two parallel patterns, interacted together so as to form a single three-dimensional structure, when contacting together. Without to be bound by any theory, the Applicant believes that the shape of the three-dimensional actin structure resulting from the interaction of two actin substructures could be fully-controlled by the shape of the patterns as well as by the initial molar ratios between actin monomers, Arp2/3 complex and capping protein.

Noteworthy, the applicant showed that three types of three-dimensional actin structures may be obtained by interacting together two actin substructures, namely (i) three-dimensional structure of the "column type" (or having a "I"-shape), (ii) three-dimensional structure of the "receptacle-plug type" and (iii) three-dimensional structures having a "T"-shape (see FIG. 1).

Indeed, in some cases, after two actin sub-structures growing face-to-face interact together, there is no change in the elongation orientation of their actin networks: the interaction of the two actin substructures lead to a three-dimensional structure of the "column type" or of the "receptacle-plug type" depending on the shapes of the patterns from which the two substructures have been initiated. If the two patterns have similar shape and size, the actin polymerization stops once the two substructures interact together, even if actin monomers are still present in the medium. Surprisingly, the presence of a capping agent together with a molar ratio of actin monomers to Arp2/3 generally lower than 20 diminished and even prevented the deformation of the said two actin substructures when contacting together contrary to what observed without capping agent. The resulting three-dimensional actin structure has thus a "I"-shape or the shape of a "column" (see FIG. 4). For example, a three-dimensional actin structure having the shape of a cylinder or a rectangular cuboid may be obtained from round patterns or square patterns, respectively.

Figure 3:
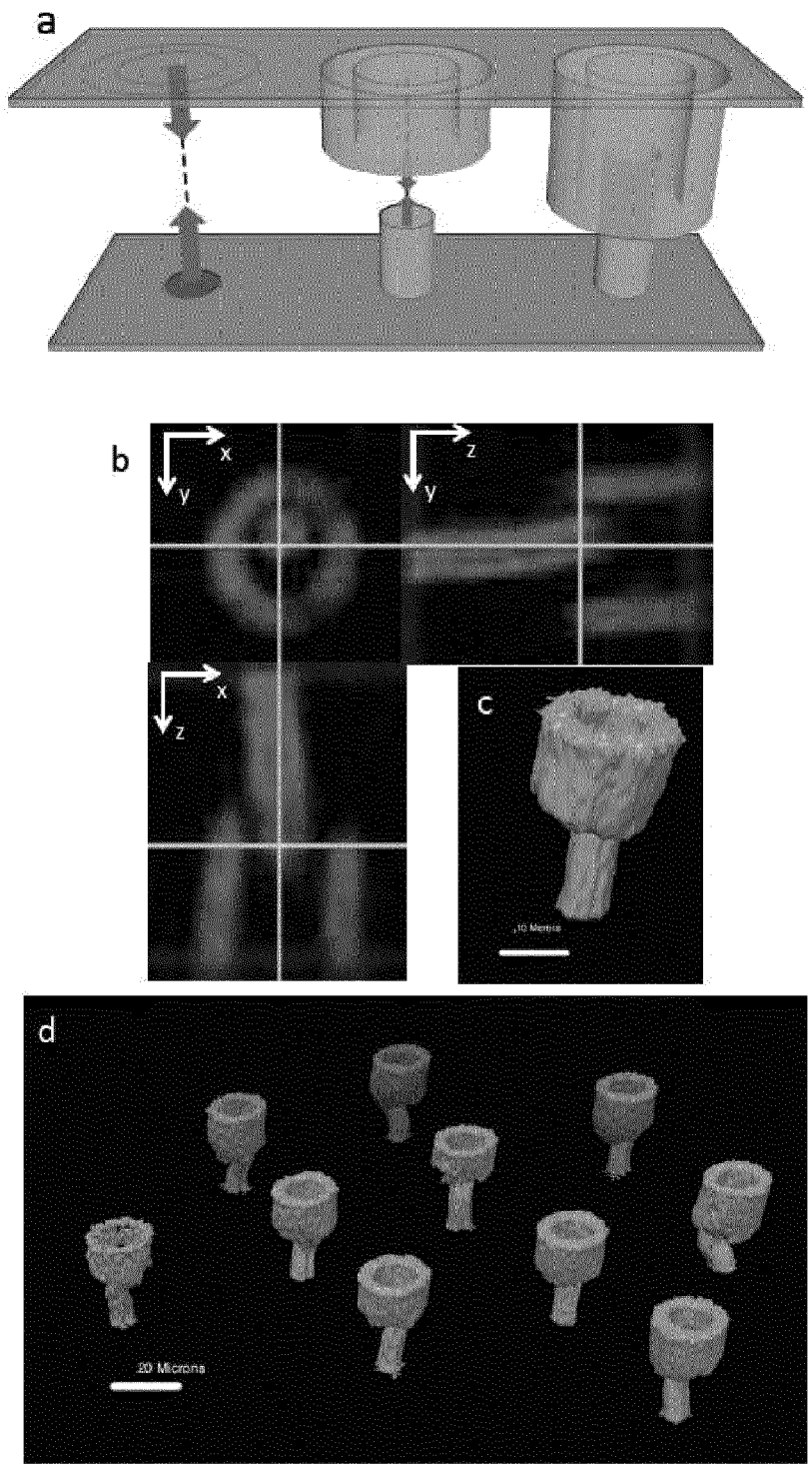
FIG. 3 shows the creation of a plurality of three-dimensional actin structures of "the plug-receptacle type".

If the two face-to-face patterns have complementary shapes such as a large empty circle and a filled disk having a radius smaller than that of the circle, a three-dimensional actin structure of the "receptacle-plug" type may be obtained as illustrated in FIG. 3B. In such a case, the actin network from the largest pattern partially surrounds the network from the smallest pattern. Surprisingly, the two actin substructures retain their form even after interacting together.

Figure 5:
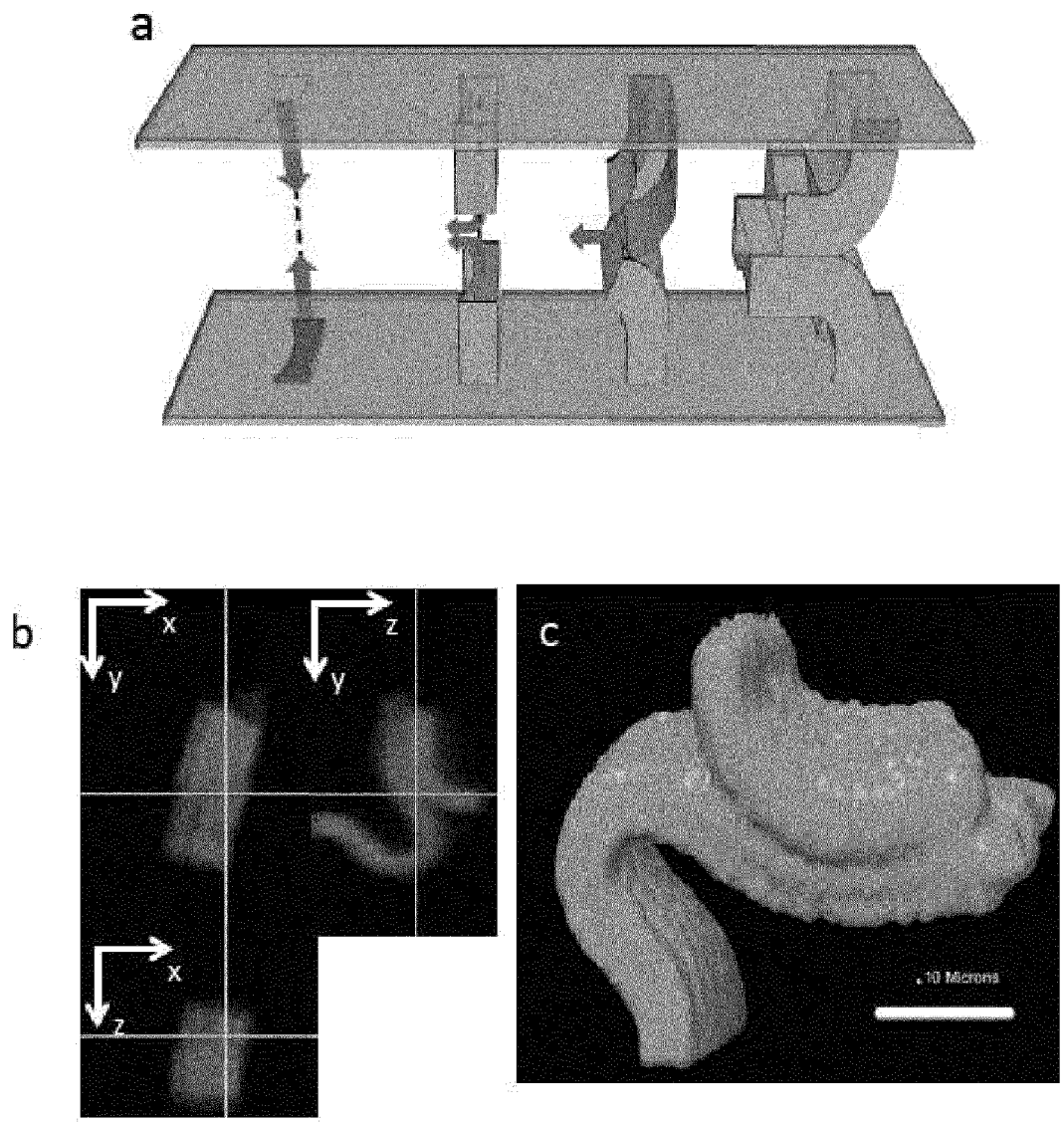
FIG. 5 shows the formation of a three-dimensional structure having T-shape.

In some other cases, after the two actin substructures growing face-to-face interact together, there is a change in the elongation orientation of their two actin networks such that a three-dimensional actin structure having a "T-shape" is finally obtained (see FIG. 5). Indeed, the two actin networks, which have grown face-to-face, interact together and continue their elongation in a plane parallel to the two patterns (from which they have been initiated) and in the same direction. In such a case, the molar ratio of actin monomers to Arp2/3 is generally higher than 20.

The direction of elongation may be controlled by the shape of the two patterns. Accordingly, if the two patterns are similar and have a rectangular shape, the elongation of the two networks is generally observed in a direction perpendicular to the length of the patterns. In the same way, if the patterns are half circles or quarter circles, the elongation may be observed in a direction opposite to the arcs of circle of the patterns.

Noteworthy, the method of the invention enable to obtain filled or empty three-dimensional structures depending on the shape of the original patterns. The resulting three-dimensional actin is of the nanometer scale or of the micrometer scale. In all cases, the said structure is composed of a highly-branched and dense network of short actin filaments.

As described further below, the method for preparing a three-dimensional actin structure according to the invention may be useful in various nanotechnology fields, in particular in microelectronics, for creating nano- or micro-electrical connections between silicon wafers.

Method for Preparing a Three Dimensional Structure of Actin

A first object of the present invention is a method for preparing a three dimensional structure of actin of the nano- or the micrometer scale. This method requires:
(i) a polymerization solution able to promote actin polymerization, and
(ii) at least one surface having thereon a pattern coated with a nucleating agent.

The polymerization of the three-dimensional actin structure occurs by contacting the patterned surface with the polymerization solution.

On one hand, the pattern present on the surface enables to fully-control the location of actin polymerization (which is confined on the pattern) and is a determining factor of the shape of the final actin structure. On the other hand, the polymerization solution has a direct impact on both the growth orientation of actin network and the mechanical properties of the final three-dimensional structure.

As mentioned previously, the polymerization solution comprises a combination of a capping agent and a branching agent. Such a combination has been shown to be essential for obtaining three-dimensional actin structures having appropriate shape, orientation and mechanical properties. It goes without saying that the said polymerization solution also comprises actin monomers. Accordingly, the method according to the invention comprises the steps of:
a. Providing a polymerization solution comprising actin monomers, a branching agent and a capping agent,
b. Providing at least one surface having thereon a pattern which is coated with a nucleating agent,
c. Contacting the at least one surface of step (b) with the polymerization solution of step (a) so as to induce the polymerization of actin and obtain the said three-dimensional actin structure.

In some embodiments, in step (b), one surface having thereon at least one pattern is provided.

In some other embodiments, in step (b), a first and a second surfaces are provided, each surface having thereon a pattern coated with a nucleating agent, the said first and second surfaces being positioned so that:
- the said surfaces are substantially parallel,
- the pattern of the first surface and that of the second pattern are face-to-face,
- the center of the pattern of the first surface is substantially aligned with that of the pattern of the second surface, and
- the distance between the first surface and the second surface is at most 1 mm.

In such embodiment, during step c), the pattern of the first and that of the second surface are simultaneously contacted with the polymerization solution. Indeed, the first and the second surfaces may be two inner surfaces of a reaction chamber which may be filled with the polymerization solution or in which the polymerization solution may flow thanks to appropriate circulation means. During step c), the actin polymerization simultaneously occurs from the pattern of the first surface and from the pattern of the second surface, since the two patterns are in contact with the polymerization solution. Accordingly, two three-dimensional actin substructures, one from the pattern of the first surface and one from the pattern of the "opposed" second surface, grow face-to-face and then interact together so as to form the desired three-dimensional actin structure. As mentioned previously, various three-dimensional actin structures may be obtained by this method depending on the pattern shapes and the composition of the polymerization solution. This embodiment enables to obtain complex actin architectures such as three-dimensional structures of the receptacle-plug type, three-dimensional structures of the column type or three-dimensional structures having a T-shape.

Indeed, the method of the invention is further characterized in that the shape of the final three-dimensional structure is controlled by the geometry of the pattern(s) present on the said surface(s) and by the molar ratios of the branching agent to the actin monomer and to the capping agent.

By two surfaces which are substantially parallel, it is meant that the two surfaces are positioned such that they form an angle of less 5°, preferably less than 2° (in absolute value). In some embodiments, the two surfaces are parallel.

The centers of the two patterns are substantially aligned means that the centers of the two patterns are disposed on a line which is substantially perpendicular to the first surface comprising thereon the first pattern. A line substantially perpendicular to a surface means that the said line forms an angle ranging from 80° to 90°, preferably from 85° to 90°, and more preferably an angle ranging from 88° to 90°, with any one of the lines comprised within the plane defined by the said surface.

The two surfaces are substantially planar, preferably planar.

Figure 4:
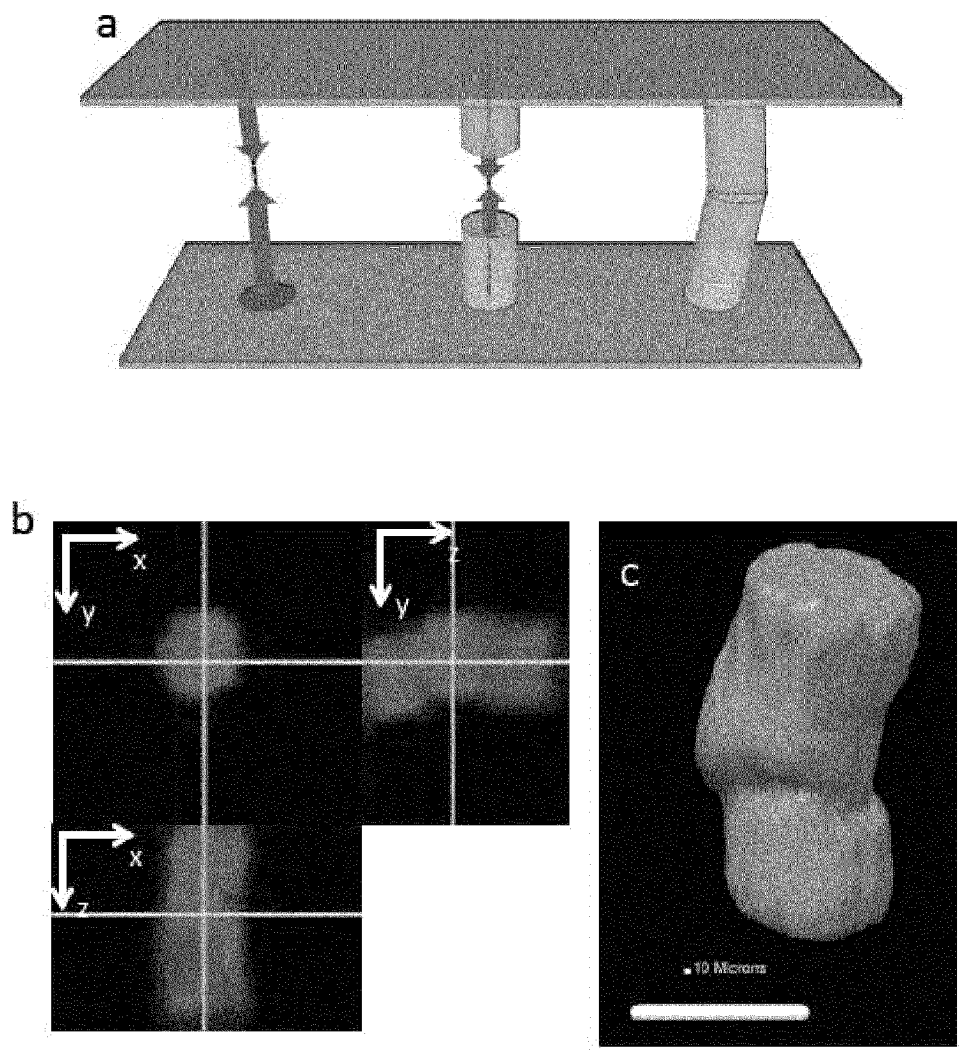
FIG. 4 shows the three-dimensional structure of the "column type" and illustrates that face-to-face patterns do not need to be perfectly aligned to obtain a three-dimensional structure.

For obtaining a final structure of "the column type" or having a "T-shape", the centers of the two patterns do not need to be perfectly aligned to obtain the desired structure since the two face-to-face growing sub-structures are able to properly interact together even if the patterns are not well-aligned. Such a fact is illustrated by FIG. 4. Noteworthy, in the case of T-shape structure, the two patterns may be shifted from a perfect alignment by a shift of at most equal to the width of the smallest pattern.

For obtaining a final structure of "the plug-receptacle", it may be preferable that the centers of the patterns are perfectly aligned. In some embodiments, the centers of the pattern are aligned, namely vertically or horizontally aligned depending on the positioning of the two surfaces.

The distance between the two patterned surfaces may be up to 1 mm. Preferably, the distance between the two surfaces ranges from 1 µm to 900 µm. A distance ranging from 1 µm to 900 µm encompasses a distance ranging from 1 µm to 50 µm, a distance from 50 µm to 100 µm, a distance from 100 µm to 200 µm, a distance from 200 µm to 300 µm, a distance from 300 µm to 400 µm, a distance from 400 µm to 500 µm, a distance from 500 µm to 600 µm, a distance from 600 µm to 700 µm, a distance from 700 µm to 800 µm, a distance from 800 µm to 900 µm. A distance from 1 µm to 50 µm encompasses a distance from 1 µm to 10 µm, from 10 µm to 20 µm, from 20 µm to 30 µm, from 30 µm to 40 µm and from 40 µm to 50 µm. Such a distance further encompasses a distance from 5 µm to 45 µm or from 10 µm to 40 µm.

The said distance generally depends on the size of the patterns and the contemplated height for the final structure. The physical aspect ratio of the final structure may generally be up to 10. A physical aspect ratio up to 10 encompasses a physical ratio up to 1, up to 2, up to 3, up to 4, up to 5, up to 6, up to 7, up to 8 and up to 9. Typically, the aspect ratio may be from 2 to 8.

The physical aspect ratio refers to the ratio of the width (i.e the smallest dimension of the pattern, in other words the dimension of the pattern along its transversal axis) and the height of the final actin three-dimensional structure. For example, from patterns having a width of 20 µm, the method of the invention enables to obtain actin structures having a height up to 200 µm. In other words, the ratio of the distance between the two patterned surfaces to the width of the largest pattern may be up to 10.

As used herein, the width refers to the dimension of the pattern along its transversal axis. For example, the width of a circle or a disk is its diameter, the width of a square is its side, the width of an ellipse corresponds to its minor diameter and the width of a rectangle is its smallest side.

In preferred embodiments, the distance between the two patterned surfaces is constant during all the polymerization process.

For each step of the process, further embodiments are described hereunder.

Polymerization Solution Providing in Step a)

The polymerization solution used in the method according to the invention comprises actin monomers, a capping agent and a branching agent. It goes without saying that the polymerization solution may comprise one or several additional elements such as ATP and a divalent cation which may be required for actin polymerization. Divalent cations encompass $Ca^{2+}$ and $Mg^{2+}$. Depending on the concentration of actin monomers and that of the branching agent, the one skilled in the art will be able to determine the appropriate amounts of ATP and divalent cations to be used.

Preferably, the branching agent is an Arp2/3 complex as defined previously in part entitled "Definition". For example, an Arp2/3 complex from mammals, e.g. from bovine brain or thymus, may be used.

The capping agent may be any appropriate protein or protein complex able to bind in vitro the barbed end of actin filament, thereby preventing the addition or the loss of actin subunits from the said end. In some embodiments, the capping agent further has a dissociation constant (Kd) for the barbed end of actin filament lower than 1 µM, preferably lower than 100 nM, lower than 50 nM and even lower than 10 nM. Kd of the capping agent for F-actin filament is preferably determined as described above in "Definition" section.

Capping agent includes, without being limited to, Capping Proteins, gelsolin, Cytochalasin D, Eps8,Abp1 and Aim3 and ADF/cofilin in combination with Aip1, FH2 domain of formins, variants, combinations and fragments thereof. Preferably, the capping agent is selected from the group consisting of Capping Proteins αβ, fragments, variants and combinations thereof. For example, an appropriate Capping protein is a capping protein from mammals such as the Mouse Capping Protein αβ.

The presence of the capping agent is crucial to promote the growth of the actin filaments perpendicularly to the surface of the pattern. As above-mentioned, the molar ratio of Arp2/3 to the capping agent may also have a direct impact on the efficiency of the process according to the invention.

Accordingly, in a preferred embodiment, the molar ratio of Arp2/3 complex to the capping agent ranges from 0.1 to 4.

A molar ratio of Arp2/3 complex to capping agent ranging from 0.1 to 4 encompasses a molar ratio of 0.1, 0.2, 0.3, 0.4, 0.5, 0.6, 0.7, 0.8, 0.9, 1, 1.1, 1.2, 1.3, 1.4, 1.5 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, and 4.0. A molar ratio higher than 4.0 leads to a three-dimensional structure having a poor mechanical rigidity. On the contrary, a molar ratio lower than 0.1 drastically prevents the growth of the actin network from the pattern. A molar ratio from 0.1 to 4.0 encompasses a molar ratio from 0.1 to 1.0, a molar ratio from 1.0 to 2.0, a molar ratio from 2.0 to 3.0, a molar ratio from 3.0 to 4.0, a molar ratio from 0.5 to 1.5, a molar ratio from 1.5 to 2.5, a molar ratio from 2.5 to 3.5.

In some embodiments, the said molar ratio ranges from 0.5 to 3.0. In other embodiments, the said molar ratio ranges from 1.0 to 2.5. In some additional embodiments, the said ratio ranges from 0.5 to 1.0.

It should be noted that the molar ratio of Arp2/3 complex to the capping agent may slightly vary depending on the specific activity of the Arp2/3 complex and that of the capping agent. The activity of Arp2/3 complex and that of the capping agent may vary upon their purity rate and their origin. The hereabove mentioned ratios are given for fully-active Arp2/3 complex and Capping proteins.

The concentration of the capping agent within the polymerization solution is generally at least $1.10^{-9}$ mol·l$^{-1}$. A concentration of the capping agent lower than $1.10^{-9}$ mol·l$^{-1}$ is generally not sufficient to fully-control the growth orientation of actin filaments and to obtain a three-dimensional actin structure with appropriate shape and rigidity. A capping agent concentration of at least $1.10^{-9}$ mol·l$^{-1}$ encompasses a capping agent concentration of at least $5.10^{-9}$ mol·l$^{-1}$, of at least $1.10^{-8}$ mol·l$^{-1}$, of at least $5.10^{-8}$, of at least $1.10^{-7}$, of at least $5.10^{-7}$ mol·l$^{-1}$. A capping protein concentration higher than 2 μM (i.e. $2.10^{-6}$ mol·l$^{-1}$) is not preferred. Generally the capping agent concentration ranges from 1 nM to 1 μM.

In some embodiments, the concentration of the capping agent in the polymerization solution ranges from 5 nM to 200 nM.

A concentration of capping agent ranges from 5 nM to 200 nM encompasses a concentration of capping agent ranging from 5 nM to 10 nM, a concentration of capping agent ranging from 10 nM to 30 nM, a concentration of capping agent ranging from 30 nM to 60 nM, a concentration of capping agent ranging from 60 nM to 100 nM, a concentration of capping agent ranging from 100 nM to 150 nM, a concentration of capping agent ranging from 150 nM to 200 nM.

Accordingly, in an embodiment of the method according to the invention, the polymerization solution is characterized by:

A molar ratio of Arp2/3 to capping agent ranging from 0.1 and 4.0, preferably from 0.3 and 2.0, and A capping agent concentration of at least 1 nM, preferably of at least 10 nM, and more preferably from 10 nM to 100 nM.

The concentration of actin monomers in the polymerization solution is higher than that of the capping protein and the Arp2/3 complex. Accordingly, the molar ratio of actin monomers to Arp2/3 may range from 5 to 500. A ratio ranging from 5 to 500 encompasses a ratio of 5, 10, 15, 20, 25, 30, 35, 40, 45, 50, 55, 60, 65, 70, 80, 90, 100, 120, 140, 160, 180, 200, 240, 280, 320, 360, 400, 440, 480 and 500. A ratio ranging from 5 to 500 encompasses a ratio from 5 to 50, a ratio from 50 to 100, a ratio from 100 to 150, a ratio from 150 to 200, a ratio from 200 to 250, a ratio from 250 to 300, a ratio from 300 to 350, a ratio from 350 to 400, a ratio from 400 to 450, a ratio from 450 to 500.

A ratio higher than 500 leads to an unfolded structure with a low rigidity. In some embodiments, the molar ratio of actin monomers to Arp2/3 ranges from 5 to 100. In some additional embodiments, the said molar ratio ranges from 30 to 50. In some additional embodiments, the said molar ratio ranges from 5 to 20.

Indeed, the molar ratio of actin monomers to Arp2/3 complex may vary depending on the three-dimensional structure to be achieved.

If the final three-dimensional structure is obtained by the interaction of two actin substructures which have grown face-to-face, a molar ratio ranging from 5 to 20 is preferred for obtaining a final structure of the "receptacle-plug type" or of the "column type". On the other hand, a molar ratio higher than 20 is preferred in order to obtain a final structure of the "T-shape" type. In that respect, a molar ratio from 20 to 50 may be generally appropriate for obtaining the said structure with "T-shape".

If the final three-dimensional structure is obtained from a single pattern, there is no restriction with respect to the molar ratio of actin monomers to Arp2/3 complex, except that it should range from 5 to 500. An appropriate ratio generally ranges from 10 to 90 and may be about 40-60, typically about 50.

The concentration of Arp2/3 complex generally ranges from 0.1 nM to 5 μM, preferably from 1 nM to 500 nM. The concentration of Arp 2/3 may be typically from 10 nM to 100 nM.

The concentration of actin monomers may vary depending on the size and the number of the three-dimensional actin structures to prepare. Generally, the concentration of actin monomers varies from 0.01 μM to 100 μM, preferably from 0.1 μM to 10 μM.

The one skilled in the art will be able to adjust the concentrations of Arp2/3, actin monomers and capping agent in order to obtain the desired three-dimensional actin structure by implementing routine experiments. It goes without saying that the quantities of actin monomers (i.e. the number of moles) may vary upon the size of the desired three-dimensional actin structure.

Actin monomers to be used in the method according to the invention may be labeled actin monomers. The label may be a fluorescent protein or a dye. Examples of fluorescent protein or dye include, but are not limited thereto, fluorescent dyes such as the Alexa Fluor dyes (e.g., Alexa 350, Alexa 430, Alexa 488, Alexa 532, Alexa 546, Alexa 568, and Alexa 594 dyes), cyanin dyes (e.g., Cy3 and Cy5), Texas Red, acyrolodan, pyrene and the like, and fluorescent proteins such as GFP, CFP, YFP, RFP and mCherry. Preferably, fluorescent dyes will be used. Some fluorescently labeled actin monomers are commercially available (e.g., non-exhaustively, Invitrogen: Alexa 488 conjugate (Cat. No.: A12373), Alexa 568 conjugate (Cat. No.: A12374), Alexa 594 conjugate (Cat. No.: A34050) and Alexa 647 conjugate (Cat. No.: A34051)). Actin monomers may be also labeled with a metal atom or with an inorganic molecule. For example, the actin monomer may be bound to a metal atom such as gold or to a quantum dot. In that respect, Patolsky et al. (Nature Materials, 2004, 4, 692-695), the disclosure of which is incorporated herein by reference, describes a method for obtaining G-actins labelled with Au atoms. Accordingly, the polymerization solution may include, with respect to actin monomers, (i) only labeled actin monomers, (ii) only unlabeled actin monomers or (ii) a mixture of labeled actin monomers and unlabeled actin monomers.

The polymerization solution also comprises an agent able to prevent the spontaneous polymerization of actin monomers in solution. In the presence of such an agent, the growth of actin filaments is mostly (and even only) observed from the nucleating sites present on the pattern of the surface. A preferred agent is profilin, fragment and variant thereof. Profilin from any source may be added in the polymerization solution according to the invention. The concentration of profilin in the polymerization solution may be adjusted in view of the actin monomer concentration. Typically, the molar ratio of profilin to actin monomers ranges from 0.1 to 20, preferably from 1 to 10 and more preferably from 2 to 5.

A molar ratio of profilin to actin monomers from 2 to 5 includes a molar ratio from 2 to 2.5, a molar ratio from 2.5 to 3.0, a molar ratio from 3.0 to 3.5, a molar ratio from 4.0 to 4.5, a molar ratio from 4.5 to 5.

For example, for an actin monomer concentration of 3 µM, profilin may be used at a concentration of about 6 µM to 15 µM.

An appropriate ratio of profilin to actin monomer is a ratio of about 3.

Noteworthy, even if profilin prevents the spontaneous polymerization of actin in solution, few short actin filaments (comprising e.g., 2-4 monomers) are still formed in the polymerization solution. These short actin filaments are sufficient to initiate actin polymerization from the nucleating site when the patterned surface is contacted with the polymerization mix. In other words, it is not necessary to specifically add, within the polymerization solution, one or several actin filaments in order to initiate the polymerization of actin filament by the polymerization system composed of (i) the Arp2/3 complex from the polymerization solution and (ii) the nucleating agent immobilized on the pattern.

However, even if it is not necessary for implementing the method of the invention, actin filaments having a length from 30 nm to 300 nm may nevertheless be added in the polymerization solution at a concentration ranging from 0.1 nM to 1 µM.

In some embodiments, the polymerization solution may further comprise a cross-linking protein as described above in the "Definition section". For example, the cross-linking protein may be actinin α, fascin or a combination thereof.

The molar ratio of cross-linking proteins to Arp2/3 complex is preferably of at most 5. A ratio higher than 5 may drastically impairs the growth of actin network by too tightly binding actin filaments together. A molar ratio of at most 5 encompasses a molar ratio ranging from 0.1 to 0.5, a molar ratio ranging from 0.5 to 1.5, a molar ratio ranging from 1.5 to 2.5, a ratio ranging from 2.5 to 3.5, a molar ratio ranging from 3.5 to 4.5.

The adding of a cross-linking protein within the polymerization solution may increase the mechanical rigidity of the final three-dimensional actin structure by creating connections between actin filaments. The presence of a cross-linking protein within the polymerization solution may also help to create more stable connections between two actin substructures growing face-to-face so as to form a single three-dimensional structure.

Accordingly, cross-linking proteins are generally not required during the polymerization process for obtaining the structure having "T-shape" as described above. If present, the molar ratio of said proteins to Arp2/3 complex may be lower than 1, preferably lower than 0.5. Similar molar ratio is also preferred for preparing three-dimensional structure of the "receptacle-plug type"

The presence of cross-linking proteins during polymerization process may be advantageous for preparing an actin structure of the "column shape" since it may enhance the binding between the two face-to-face growing actin substructures so as to provide a single structure displaying high cohesion. In this context, a molar ratio ranges from 0.5 to 4.5 is generally appropriate.

In some further embodiments, the polymerization solution may comprise an agent able to stabilize actin structure and/or to inhibit actin depolymerization. Such an agent may be phalloidin or an analog thereof. The molar ratio of actin monomer to the said agent may be from 0.1 to 10. Typically, such an agent may be used at a concentration from 0.1 µM to 10 µM, e.g. from 0.5 µM to 5 µM.

The polymerization solution may further comprise one or several optional agents. These optional agents include, without being limited to, actin polymerization regulators, fragments or mutants thereof.

Are used herein, actin polymerization regulators refer to regulator proteins which may be required for actin polymerization depending on the nature of the nucleating agents immobilized on patterns. Some actin nucleation agents like ActA, IscA, RickA, WASp, N-WASP and SCAR may require the presence of a protein such as Cdc42, PIP2, Nck and Rac for initiating the actin polymerization in the presence of Arp2/3. Those requirements are well-known in the art and, for instance, are detailed in US 2006/003399 and Higgs and Pollard, 2001, Annu Rev Biochem., 70, 649-76.

The polymerization solution according to the invention does not comprise any proteins selected from spire proteins and formins. Formins and spire proteins are able to initiate and promote the polymerization of actin filaments and are reviewed in Baum and Kauda (Current Biology, 2005, 15, R305-R308) and in Kovar (Current Opinion in Cell Biology, 2006, 18, 11-17). The presence of these proteins is not required in the polymerization solution due to the presence of Arp2/3 complex and may be even detrimental for implementing the method according to the invention.

In some specific embodiments of the method according to the invention, the polymerization solution comprises actin monomers, an Arp2/3 complex, a capping agent, ATP, a divalent cation and profilin and is characterized by a molar ratio of Arp2/3 to capping agent ranging from 0.1 and 4.0.

The said polymerization solution may be further characterized by one or several (2, 3, 4, 5, 6, or 7) following features:
   The molar ratio of actin monomers to the Arp2/3 complex ranges from 5 to 500, preferably from 5 to 100;
   The concentration of actin monomers ranges from 0.01 µM to 100 µM;
   The concentration of the capping agent ranges from 1 nM to 1 µM
   The molar ratio of profilin to actin monomers ranges from to 0.1 to 20, preferably from 1 to 10;

A fraction of actin monomers present in the polymerization solution is labeled;

The polymerization solution comprises a cross-linking protein, preferably actinin α and/or fascin, the molar ratio of the said cross-linking protein to Arp2/3 complex being at most 5, and/or, The polymerization solution comprises an agent able to stabilize actin structure and/or to inhibit actin depolymerization, such as phalloidin It goes without saying that the polymerization solution may be prepared from any conventional buffer at a pH suitable for the activity of the proteins present within the said polymerization solution (e.g. HEPES at pH 7-8).

Nucleating Agent Immobilized on Surface Pattern(s) of Step (b)

The immobilized nucleating agent should be able to initiate actin polymerization in a branching agent-dependent manner. Accordingly, if the polymerization solution comprises a Arp2/3 complex as branching agent, the pattern should be coated with a nucleating agent or a mixture of nucleating agents able to initiate actin polymerization in the presence of Arp2/3 complex. Examples of nucleating agents able to interact with Arp2/3 complex, include, without being limited to, nucleating agents cited hereabove in the part entitled "Definitions" as well as in Goley and Welch, Nature Reviews, 2006, 7, 713-726, the disclosure of which is incorporated by reference. Appropriate nucleation agents also include analogues (chimeric forms or mutants) and fragments thereof capable of initiating actin polymerization in the presence of Arp2/3 complex.

In some embodiments, the nucleating agent is selected from the group consisting of members of the WASp family, members from SCAR/WAVE family, VCA domains thereof, peptides from VCA domains such as WA and pWA, functional homologs of SCAR/WAVE and WASp proteins such as ActA from *Listeria* and RickA from *Rickettsia*, and combinations thereof.

As mentioned previously, some actin nucleation agents like ActA, IscA, RickA, WASp, N-WASP and SCAR proteins may require additional regulating proteins or elements (also called upstream regulators) such as Cdc42, PIP2, Nck and Rac1. These regulating proteins may be present in the polymerization solution as mentioned previously or in the pattern coating.

VCA (also called WCA) refers to verprolin homology, cofilin homology and acidic region) domain. A pWA peptide is a fragment of VCA domain. It corresponds to the C-terminal domains of SCAR/WAVE or WASp proteins and includes the proline rich domain, the actin monomer binding W domain, and the p21-binding A domain. In particular, pWA may comprise or consist of amino acids 172-559 of human SCAR protein (SEQ ID No 1) (Machesky et al, 1999, PNAS, vol. 96, no. 7, 3739-3744).

Indeed, the use of a pWA peptide or a VCA domain is advantageous over the other nucleating agents because it does not require the use of upstream regulators. In a preferred embodiment, the nucleating agent is selected from pWA fragments and VCA domains from proteins belonging to SCAR/WAVE and WASp families polypeptides, variants thereof and combinations thereof.

In some embodiments, the nucleating agent is selecting from a polypeptide comprising an amino acid sequence having at least 80% identity with the amino acid sequence of SEQ ID No 1. A sequence identity of at least 80% encompasses a sequence identity of at least 85%, of at least 90%, of at least 95%, of at least 98%, of at least 99%.

The nucleating agent may comprise one or several tag(s), preferably linked or fused to the amino and/or carboxyl terminal ends. These tags are introduced either for improving the expression, the solubility or the purification of said nucleating agent during its manufacture process or for enabling the immobilization of said nucleating agent onto a surface. In a particular embodiment, the actin nucleating agent is a pWA domain comprising two tags, for example, a GST tag at its N terminal end and an His tag at its C terminal end.

Patterns and Patterned Surfaces of Step (b)

As mentioned above, the pattern may be coated by a nucleating agent or a mixture of nucleating agents as defined above. The pattern may optionally comprise regulating proteins which may be required depending on the nucleating agent used.

The nucleating agent is generally the sole molecule present on the pattern able to control the location of actin polymerization. In particular, the pattern may be devoid of agents able to capture actin monomers or actin filaments such as myosin, N-ethylmaleimide-myosin, phalloidin, alpha-actinin and fascin.

In particular, in the embodiments wherein the final actin structure results from the interaction of two actin substructures which have grown face-to-face, the pattern immobilized on the first surface and that immobilized on the second surface are devoid of agents able to capture actin monomers or actin filaments such as myosin, N-ethylmaleimide-myosin, phalloidin, alpha-actinin and fascin.

The density of nucleating agents which are immobilized on the pattern enable to obtain a density of actin branches of at least 10 branches by $\mu m^2$ which encompass a density of at least 10, 20, 30, 40 and 50 branches per $\mu m^2$. Generally, the pattern is fully-coated with nucleating agent and as a consequence, the factor controlling the density of actin branches is rather Arp2/3 concentration.

The pattern(s) present on the surface may be of any shape and any size. Indeed, the shape of the patterns depends on the desired final three-dimensional structure(s).

The pattern may be a filled or an empty shape.

Examples of appropriate pattern shapes include, without being limited to, lines, curves, circles, polygons and ellipses and combinations thereof. Polygons encompass triangle, quadrilaterals such as parallelograms, squares, rectangles and rhombus, pentagons, hexagons and the like. The largest dimension of the pattern may be of the nanometer scale or the micrometer scale. Generally, the longitudinal dimension of the pattern may range from 50 nm to 1 mm, preferably from 100 nm to 300 μm.

The pattern may be (i) of the nanometer scale on its two dimensions or (ii) of the micrometer scale on its two dimensions. In some particular embodiments, the pattern may be of the nanometer of scale for one of its dimension and of the micrometer scale for its other dimension. For example, the pattern may be a rectangle with width of the nanometer scale and length of the micrometer scale.

Figure 6A:
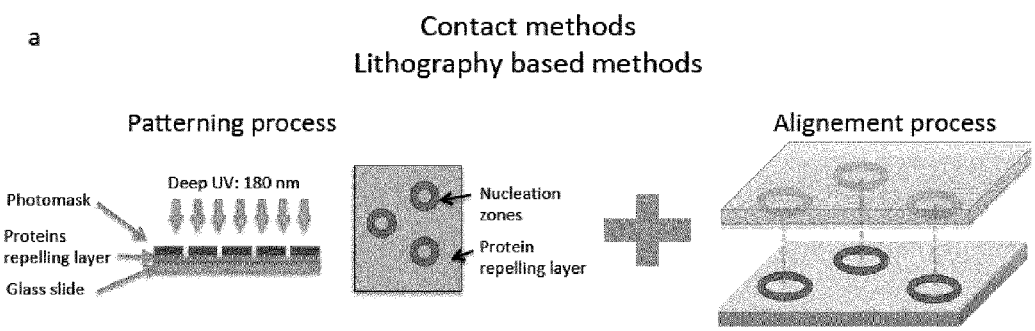
FIGS. 6A and 6B show two patterning methods which may be used in the context of the present invention. The patterning of the surfaces can be done either with a contact patterning method followed by an alignment step (FIG. 6A) or by a non-contact patterning method such as a laser based patterning method (FIG. 6B). In that case, the surfaces are assembled before the patterning process and the patterns are directly aligned thanks to the non-contact patterning method.

As used herein, an empty pattern means that the pattern defines an outline surrounding an inside area which is not coated with nucleating agent. An example of empty pattern is a circle as illustrated in FIG. 6A. The thickness of the pattern outline may vary upon the size of the pattern and the final pattern desired. Generally, the thickness of the outline may vary from 50 nm to 100 μm. For example, for obtaining an empty actin cylinder having a radius of 5 μm and a wall thickness of 1 μm, the pattern to be used should be an empty circle having a radius of 5 μm and an outline thickness of 1 μm. Depending on the structure to be achieved, the one skilled in the art would determine the appropriate pattern(s) to be used. Generally, the outline thickness of empty patterns may range from 1 to 6 µm, preferably from 2 µm to 4 µm.

Accordingly, a filled pattern does not surround any uncoated area.

When two surfaces are provided in step b), the shapes of the patterns may have a direct impact on the three-dimensional actin structure resulting from the interaction of two substructures which have grown face-to-face.

For obtaining a three-dimensional structure of the "column-type", the two face-to-face patterns may have a similar size and a similar shape. For example, the patterns may be selected from empty or filed ellipses, circles, rhombus and regular polygons. Regular polygons refer to polygons which are equilateral and equiangular such as equilateral triangle, square, pentagon, hexagon and the like. Preferably, the two patterns are filled patterns.

As used herein, by two patterns having a similar size, it means that the area delimited by the outline of the first pattern is about 0.9 to 1.1-fold the area delimited by the outline of the second pattern.

Alternatively, the two face-to-face patterns may be filled patterns having a similar shape but a distinct size. The ratio of the largest dimensions of the two said patterns may vary from 0.5 to 2. In this case, the resulting three-dimensional actin structure has a shape closed to that of the column-type and consisting of two stacked building blocks having distinct width. For illustrative purpose only, such a structure may be obtained from two face-to-face filled round patterns, the first pattern having a diameter of 10 µm and the second pattern having a diameter of 20 µm.

For obtaining a three-dimensional structure of the "receptacle-plug type", the shape of the first pattern may be complementary to that of the second pattern. This means that:

The first pattern is an empty pattern and the second pattern is a filled pattern, and The second pattern has a size and a shape such that it may be contained within the non-coated area surrounded by the first pattern.

In some embodiments, the two complementary patterns have the same shape. For example, the first pattern may be an empty circle having a diameter of 10 µm and an outline thickness of 2 µm, the second pattern should thus be a disk having a diameter of at most 6 µm. Similarly, if the first pattern is an empty square having a length of 5 µm and an outline thickness of 1 µM, the complementary shape should be a filled square having a length of at most 3.0 µm.

In some other embodiments, the two complementary patterns do not have the same shape. For example, the first pattern may be an empty circle having a radius of "x" and an outline thickness of "a" and the second pattern may be a filled square having a length of at most "x minus 2a".

Finally, for obtaining a three-dimensional structure having a "T-shape", the two face-to-face patterns may have a similar size and shape. The said patterns are preferably filled patterns. An appropriate pattern may have an elongated shape, i.e., the ratio of its length to its width may be at least 3. The pattern may also be a disk section such as half disks and quarter disks Each provided patterned surface may comprise one or several patterns thereon. When several patterns are present on a surface, the said patterns may have similar or distinct shapes. The said patterns may be located randomly or may be regularly disposed on the said surface. In some embodiments, the patterns may be separated by a distance sufficient to prevent interaction between the actin networks which will be formed from them. Since the actin growth orientation is fully controlled in the method according to the invention, a distance of at least 1 µm is generally sufficient to prevent interaction, except sometimes in the case of the formation of T-shaped structure since an elongation of actin network is observed in a plane parallel to the patterns.

In other embodiments, the patterns may be separated by a distance sufficient to enable interactions between the actin networks. In such an embodiment, a complex three-dimensional actin architecture comprising both horizontal and vertical blocks may be obtained by the interaction of three-dimensional structures having T-shape together or with other structures.

In some embodiments, when a first and a second patterned surfaces is provided in step b), the said surfaces may have thereon a plurality of patterns so that the center of each pattern on the first surface may be substantially aligned with that of a pattern on the second surface in step c). That is to say that for each pattern of the first surface, there is a corresponding pattern on the second surface so that the said two patterns are face-to-face. In this case, the method of the invention enables to create simultaneously a plurality of three-dimensional actin structures, each three-dimensional structure resulting from the interaction of two actin substructures which have grown face to-face from opposed patterns (for illustration see FIG. 3B).

The present invention is not limited to the particular patterns illustrated herein. Depending on the question of interest and the three-dimensional actin structure to achieve, the one skilled in the art may design other patterns.

The surface to be patterned may be any solid support having a sufficient area for disposing thereon a pattern coating with a nucleating agent as described previously.

The surface thus may be flat, wavy or curved. In some embodiments, the surface is planar or essentially planar.

The surface may be composed of any material enabling the deposition of the desired pattern. For instance, the surface may be silicon, strained silicon, polycrystalline silicon, polycrystalline silicon, silicon dioxide, germanium, gallium, arsenic, glass, plastic, ceramic, or metal. The nature of the surface may depend on its final use. As explained further below, for use in microelectronics, the surface may be a silicon wafer or a chip. If the final 3D-dimensional actin structures may be observed by optical or/and fluorescence microscopy, the surface may be a glass, eventually covered with a thin layer of oxidized polystyrene. In that respect, the surface may be a coverslip or a slide appropriate for microscopy.

For implementing the methods according to the invention, the patterned surface is preferably passivated in order to prevent non-specific adsorption of actin outside of the pattern(s). In other words, except on the actin nucleation site pattern(s), the surface is inert with respect to actin molecules. The surface may be rendered inert by coating. For example, the surface may be covered by a derivative of poly(ethylene glycol) (PEG) such as Polylysine-PEG and silane-PEG. As an alternative, other molecules and compositions commonly used in biology for reducing non-specific binding of proteins on surface may be used for creating an inert coating. Such molecules and compositions encompass non-fat milk, bovine serum albumin and human serum albumin.

The passivation of the surface may occur before or after the creation of pattern(s) thereon.

Pattern may be created onto the surface by any conventional methods described in the prior art such as microcontact printing, X-ray and e-Beam photolithography, photolithography, laser ablation, UV-based micropatterning approach (Azioune et al, 2009, Lab Chip, 9, 1640-1642), Dip Pen (Ginger et al, 2004, Angew Chem Int Ed Engl, 43, 30-45.), Atomic Force Microscopy ("AFM") subtraction (Wadu-Mesthrige et al, 2001, Biophys J 80, 1891-9), and plasma deposition.

Preferred patterning methods include (i) the passivation of the surface by the creation of an inert coating such as described previously, (ii) the removing and/or the activation of the said coating on specific locations so as to define the shape of the pattern and create sites able to bind the nucleating agent and (iii) the binding of the nucleating agent thereon.

Figure 6B:
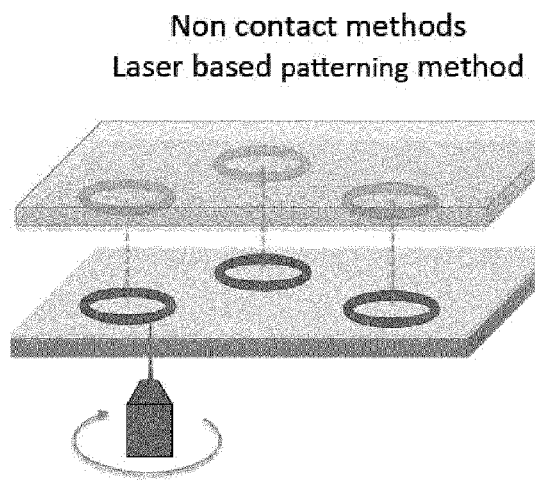

For instance, convenient protocols are detailed in FIGS. 6A and 6B. FIG. 6A illustrates a photolithography based process in which the pattern is obtained by removing the inert coating on specific locations thanks to UV treatment in the presence of a photomask. FIG. 6B (as well as the Examples of the instant application) describes an alternative process in which the shape of the pattern(s) is drawn thanks to a pulsed UV laser beam which oxidizes the coating on specific locations which are thus able to covalently bind proteins such as nucleating agents. This latter method does not require the use of a photomask and thus may be advantageously used for creating patterns onto two parallel surfaces already aligned. In this latter method, there is no need to subsequently align the patterned surfaces since the face-to-face patterns are already well-aligned.

Another appropriate method is described in Brough et al. (see supra), such a method being based on the use of e-beam photolithography.

Depending on the patterning methods, patterns of the nano- or the micrometer size may be achieved with a resolution generally below 100 nm.

In the embodiment of the invention wherein in step b) two patterned surfaces are provided so as to form the so-called actin structures of "column-type", the "receptacle-plug type" or of "the T-shape type", the two surfaces may be positioned before or after the creation of patterns thereon, depending on the patterning method.

Step c) of Contacting Patterned Surface with the Polymerization Solution and Optional Steps Step c) is merely performed by contacting the patterned surface(s) with the polymerization solution during a period sufficient for obtaining a three-dimensional actin structure having the desired height. Generally, the polymerization process may last one to several hours for obtaining one or several three-dimensional actin structures of the micrometer scale.

Other Steps of the Method According to the Invention

The method of the invention may further comprise one or several additional steps.

Indeed, Step c) of the method may be followed by one or several of the following steps of:
  A step of removing the polymerization solution once the three-dimensional actin structure has been obtained,
  A step of incubating the three-dimensional actin structure with a solution comprising a cross-linking protein,
  A step of incubating the three-dimensional actin structure with a solution comprising a chemical cross-linker, a chemical fixative agent and/or an agent able to inhibit actin depolymerization,
  A step of chemically functionalizing the three-dimensional actin structure, and/or
  A step of metallization of the three-dimensional structure.

The hereabove list of steps is not exhaustive. Further other steps may be performed depending on the use of the structure which is contemplated.

The step of incubating the three-dimensional actin structure with a solution comprising a cross-linking protein may enhance the rigidity of the final structure by linking together actin branches. Appropriate cross-linking proteins are those previously cited and encompass alpha-actinin and fascin.

The incubation of the structure with a chemical cross-linker, a chemical fixative agent or a depolymerization inhibitor aims at improving the chemical stability as well as the mechanical rigidity of said structure. This treatment enables to bind together actin branches of the network through covalent bonds. Chemical fixative agents encompass formaldehyde and glutaraldehyde. Appropriate cross-linker agents are those conventionally used in biology for covalently binding together peptides or proteins. Cross-linker agents encompass bi-functional agents able to react with amine, carboxyl, or sulfhydryl functions. A large choice of cross-linkers agents is commercially available. Agent able to inhibit actin depolymerization encompasses phalloidin.

The step of functionalizing the actin structure comprises immobilized onto the said structure chemical or biological entities through covalent binding or non-covalent binding. A large type of entities may be immobilized on the actin structure depending on the intended use. The said entities include, without being limited to, dyes, fluorophores, metal atoms, quantum dots, proteins such as enzymes, antibodies and abzymes, chemical catalysts, nanotubes, synthetic or biological polymers and the like. In some embodiments, the immobilized entities form a conductive or a semi conductive coating onto the actin structure.

For illustrative purpose only, the actin structure may be labeled with fluorescently labeled phalloidin in order to enable its observation by fluorescence microscopy. More details concerning the preferred functionalization of actin structures are described further below in the part entitled "Uses".

Specific Embodiments of the Method According to the Invention

In a specific embodiment, the method according to the present invention comprises the steps of:
  a. Providing a polymerization solution comprises actin monomers, an Arp2/3 complex, a capping agent, ATP, a divalent cation and profilin wherein the molar ratio of Arp2/3 to capping agent preferably ranges from 0.1 and 4.0.
  b. Providing at least one surface having thereon at least one pattern, the said pattern being coated with a nucleating agent selected from the group consisting of members of the WASp family, members from SCAR/WAVE family, VCA domains thereof, peptides from VCA domains such as WA and pWA, functional homologs of SCAR/WAVE and WASp proteins such as ActA from *Listeria* and RickA from *Rickettsia*, and combinations thereof
  c. Contacting the at least one surface of step (b) with the polymerization solution of step (a) so as to induce the polymerization of actin and obtain the said three-dimensional actin structure.

In some specific embodiment, the method is further characterized by:
  In step b) a first surface and a second surface are provided, wherein each surface has thereon a pattern coated with a nucleating agent and the said first and second surfaces are positioned so as that:
    the said surfaces are substantially parallel and separated by a distance of at most 1 mm, and
    the pattern of the first surface and that of the second surface are face-to-face so that their centers are aligned; and
  in step c), the two patterned surfaces of step b), are contacted with the polymerization solution of step a), so as to induce the polymerization of a tridimensional actin substructure from each said pattern, thereby the final three-dimensional actin structure results from the interaction of the said two actin substructures.

Preferably, the method of the invention is further characterized by the fact that the shape of the final three-dimensional structure is controlled by the geometry of the pattern(s) present on the said surface(s) and by the molar ratios of the branching agent to the actin monomer and to the capping agent.

The method of the invention may further comprise one, several, or all of the following embodiments:

- The molar ratio of actin monomers to the Arp2/3 complex ranges from 5 to 500, preferably from 5 to 100;
- The concentration of actin monomers ranges from 0.01 μM to 100 μM, preferably from 1 μM to 10 μM;
- The concentration of the capping agent ranges from 1 nM to 1 μM, preferably from 10 nM to 100 nM.
- The molar ratio of profilin to actin monomers in the polymerization solution ranges from to 0.1 to 20, preferably from 1 to 10;
- Actin monomers are labeled;
- The polymerization solution comprises a cross-linking protein, preferably α-actinin and/or fascin, the molar ratio of the said cross-linking protein to Arp2/3 complex being at most 5.
- The polymerization solution comprises phalloidin, and the molar ratio of actin monomers to phalloidin being preferably from 0.1 to 10,
- the capping agent is selected from Capping Proteins such as mouse Capping Protein αβ,
- the nucleating agent immobilized on the pattern is selected from the group consisting of pWA fragments and VCA domains from proteins belonging to SCAR/WAVE and WASp families, variants thereof and combinations thereof,
- the at least one surface provided in step (b) is planar or substantially planar,
- the at least one surface comprises several patterns thereon,
- the at least one surface has been passivated, preferably by coating with a PEG derivative such as Poly-lysine-PEG and silane-PEG, and
- the method comprises one or several additional steps following step c) as hereabove described.

Three-Dimensional Actin Structures and Other Objects According to the Invention

A further object according to the invention is a three-dimensional actin structure obtainable by the method according to the invention.

To the Applicant's knowledge, the three-dimensional actin structure obtained by the method of the invention is characterized by an internal structure and physical properties which have never been obtained in the prior art by in vitro procedure. These internal structure and physical properties unambiguously derive from the features of the method according to the invention.

Noteworthy, the three dimensional structure according to the invention is composed of a branched network of actin filaments, wherein the distance between two consecutive actin branch points do not exceed 1 μm and preferably ranges from 0.1 nm to 1 μm. In other words, the three dimensional actin structure is composed of interconnected actin filaments, the length between two connections ranging from 0.1 nm to 1 μm. The branched actin network of the three dimensional structure comprises capping agent molecules, preferably Capping Proteins, and branching agent molecules, preferably Arp2/3 complexes.

In some embodiments, the three dimensional structure of the invention comprises two three-dimensional actin substructures connected and/or interacted together and preferably having opposite polarities. In such an embodiment, the three-dimensional structure is obtained from the interaction of two substructures which had grown face-to-face.

In some specific embodiment, the three-dimensional actin structure obtainable, or obtained, by the method of the invention is composed of a branched network of actin filaments which comprises Capping Protein molecules and Arp2/3 complex molecules and which comprises two actin substructures of opposite polarities which are connected and/or interacted together.

Another object according to the invention is a three-dimensional actin assembly comprising a plurality of three-dimensional actin structures obtainable by the method according to the invention. The said assembly may comprise a three-dimensional structure of the column type, a three-dimensional structure of the "receptacle-plug" type and/or a three-dimensional structure having a T-shape.

Three-dimensional structure having T-shape may connect with another three-dimensional structure by its network part which has grown in a plane parallel to the patterned surface. By combining three-dimensional structures having T-shape with other structures such as column-type structures or plug-receptacle-type structures, it is possible to create three-dimensional complex assembly comprising vertical and horizontal connections. Accordingly, in some embodiments, the three-dimensional actin assembly comprises both horizontal and vertical building blocks.

Another object of the invention is a surface, preferably a planar surface comprising thereon at least one actin three-dimensional structure obtainable by the method according to the invention as defined above. In preferred embodiments, the three-dimensional actin structure is perpendicular to the said surface. The area of the surface which is in contact with the actin structure is coated with a nucleating agent, more preferably comprises a pattern coated with a nucleating agent such as pWa. The said surface is preferably selected from silicon, strained silicon, polycrystalline silicon, polycrystalline silicon, silicon dioxide, germanium, gallium, arsenic, glass, plastic, polymeric substrate, ceramic, or metal. The said surface may be contained in a device such as electronic device and microfluidic device. In some embodiments, the said surface is connected to a second surface through the said actin three-dimensional structure. In some embodiments, the said surface comprises a plurality, and even an array, of three dimensional actin structures according to the invention.

The invention thus also relates to a device comprises two surfaces substantially parallel to each other wherein the said surfaces are connected to each other by at least one three-dimensional actin structure according to the invention. In preferred embodiments, the said device is characterized by one or several of the following features:

- the two surfaces are substantially planar, preferably planar,
- the area of each surface which is in contact with the actin structure is coated with a nucleating agent, more preferably comprises a pattern coated with a nucleating agent such as pWa, and
- the said three-dimensional actin structure is composed of a branched actin network which further comprises capping agent (e.g. Capping proteins) molecules and branching agent (e.g Arp2/3 complexes) molecules and which comprises two three-dimensional actin substructures connected and/or interacted together. Preferably, the two substructures have opposite polarity. The polarity of the substructure corresponds to the global polarity of the actin filaments contained in said substructure.

The invention also relates to an assembly comprising two surfaces, the said surface being connected by at least one three-dimensional actin structure according to the invention.

Uses of the Actin Structure and the Method According to the Invention

The three-dimensional actin structures and the method for preparing them according to the invention may find a large variety of uses in nano- and micro-technologies.

As illustrated above, the method according to the invention enables to create a three-dimensional actin structure between two patterned surfaces. The resulting actin structure is thus a kind of a bridge linking together the two said patterned surfaces. Accordingly, the method according to the invention may be used, in particular, for creating connections between two surfaces. These connections may be subsequently rendered conductive or functionalized.

A specific application of the method and the three-dimensional actin structure according to the invention may be found in microelectronics for connecting together stacked silicon wafers or stacked chips. In particular, the method of the invention may be used to create vertical connections, i.e. the vertical stacking of circuits to form three-dimensional electronic chip.

Indeed, a further object of the present invention is a process for creating a conductive or a semi-conductive connection between two surfaces comprising the steps of:
  i. Preparing a three dimensional actin structure actin by a method according to the invention,
  ii. coating the three-dimensional structure of actin obtained in step i) with a conductive or semi conductive layer, and
  iii. Optionally, removing the backbone of actin.

It goes without saying that the surfaces to be connected together should be patterned as fully-described previously. In preferred embodiments, the said surfaces may be silicon wafers or chips, which may be patterned and passivated according to standard methods described hereabove. For illustrative purpose only, one may refer to Brough et al. (supra) which describes a process for patterning silicon wafers.

The step ii) enables to create onto the actin structure an uniform layer which is conductive or semi-conductive.

Semi conductive layer may be obtained by immobilizing on actin structure quantum dots (for illustration of immobilization process of quantum dots on actin, see Yao et al., Anal Bioanal Chem, 395(5):1563-6), semiconductor nanotubes or other appropriate semiconductive substances.

A conductive layer may be obtained by coating the actin structures with metal atoms or molecules such as copper, stain, iron, gold, silver, conductive or semi-conductive alloys and the like, or with conductive nanotube such as carbon nanotubes.

In some embodiments, step (ii) comprises a step in which the three-dimensional actin structure obtained in step i) is submitted to a metallization process so as to coat the said three dimensional structure of actin with a conductive metallic layer.

The metallization process may be carried out by any appropriate method described in the prior art for metallizing protein fibers. In a preferred embodiment, the metallization process is performed by an electro-less approach (also called metallization without electrode) based on the use of an auto-metallographic enhancement reagent. Such reagents are commercially available. For example, for creating a gold layer, one may use the reagent "GoldEnhance®" marketed by Nanoprobes To be performed, this method requires the introduction of metallic atoms or clusters onto the actin structures. For this purpose, actin monomers labeled with a metallic atom may be added within the polymerization solution used for preparing the actin structure in step i.). An alternative is to introduce the said metallic clusters once the three-dimensional actin structure is obtained. The said metallic clusters may be introduced by chemical reactions. For example, a solution containing appropriate metallic ions able to react with certain actin amino acid moieties may be used to introduce metallic clusters. As an alternative, one may use a solution containing gold nanoparticles linked to maleimide groups (e.g. mono maleimido Nanogold® particles, Nanoprobe) which react with thiol functions of cysteine.

Figure 7:
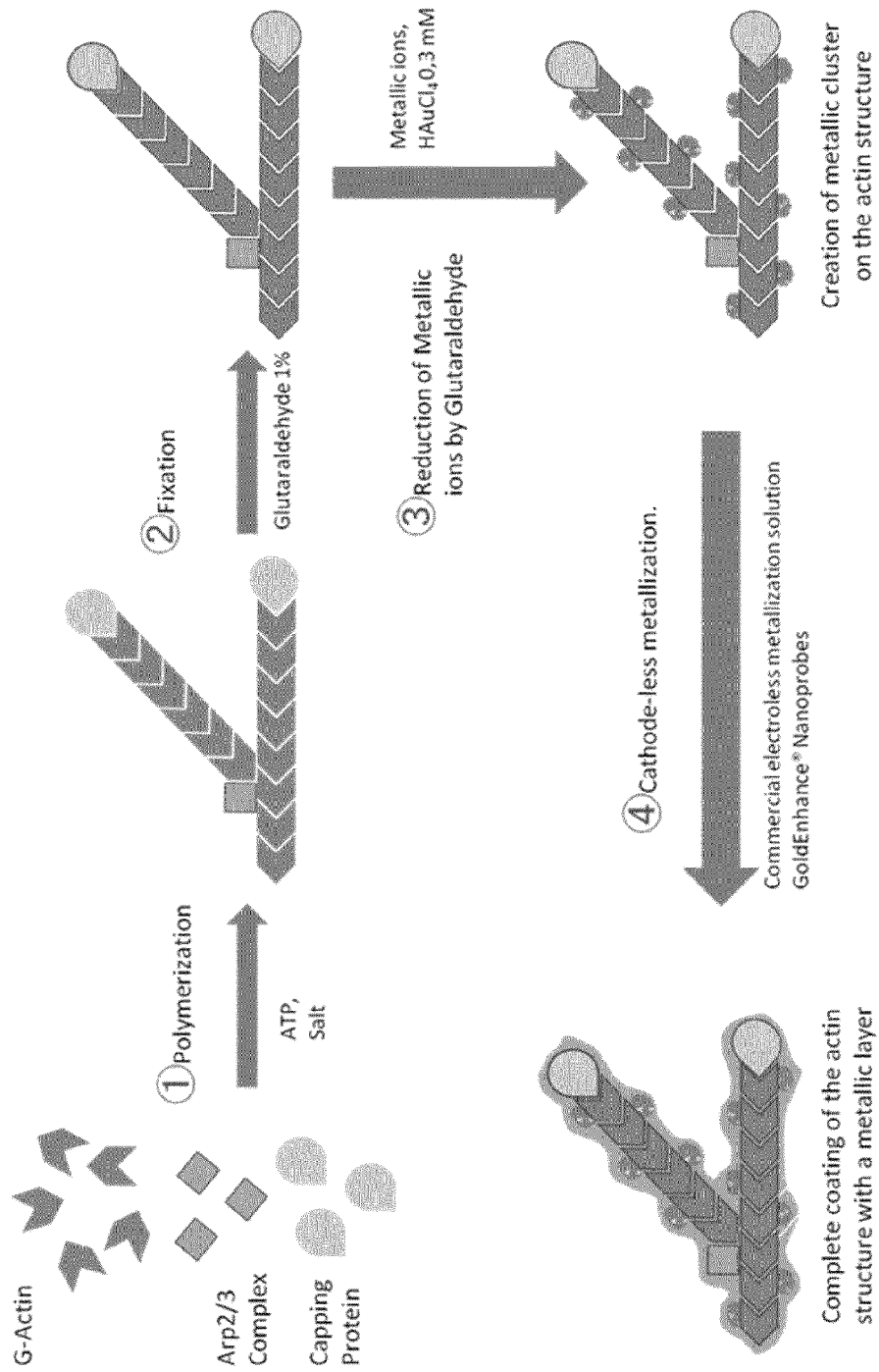
FIG. 7 shows a method for metallizing actin structures. After polymerization of actin structure, the said actin structure is fixated thanks to a Glutaraldehyde treatment. Metallic clusters are then created all along the said actin structure through the reduction of metallic ions by the glutaraldehyde moieties present on the actin structure. An electrode-less metallization based process leads then to the coating of the actin structure by a metallic layer.

For illustrative purpose only, Au clusters may be introduced by incubating the actin structure with a solution containing glutaraldehyde and then with a solution of $HAuCl_4$. Such a method is illustrated in FIG. 7.

The said metallic clusters may be also introduced by using a molecule able to bind actin such as phalloidin labeled with Au.

In some embodiments, step ii) is preceded by a step of stabilizing the three-dimensional actin structure. Such a step comprising incubating the actin structure obtained in step i) with a fixative reagent such as formaldehyde and glutaraldehyde, or with phalloidin.

The optional step iii) comprises removing the actin backbone so as to only conserve the metallic layer. The actin backbone may be removing by conventional methods such as chemical hydrolysis, enzymatic digestion and the like. In such a case, the actin three-dimensional structure is used as a sacrificial template for creating conductive connections.

Figure 8A:
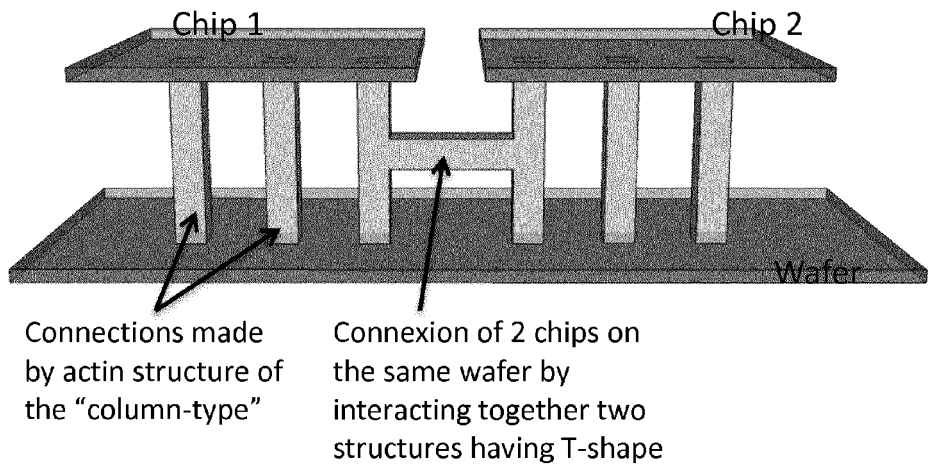
FIG. 8A shows an example of use of the method and the structure according to the invention. The method may be used for creating vertical and horizontal connections between two horizontally aligned chips situated above a common silicon wafer. Two 3D building blocks of T-shape (as shown in FIG. 8B—scale bar represents 10 µm) that are face to face are used to create a 3D connection with an H shape which enables to connect together two different chips that are on a same wafer.
Figure 8B:
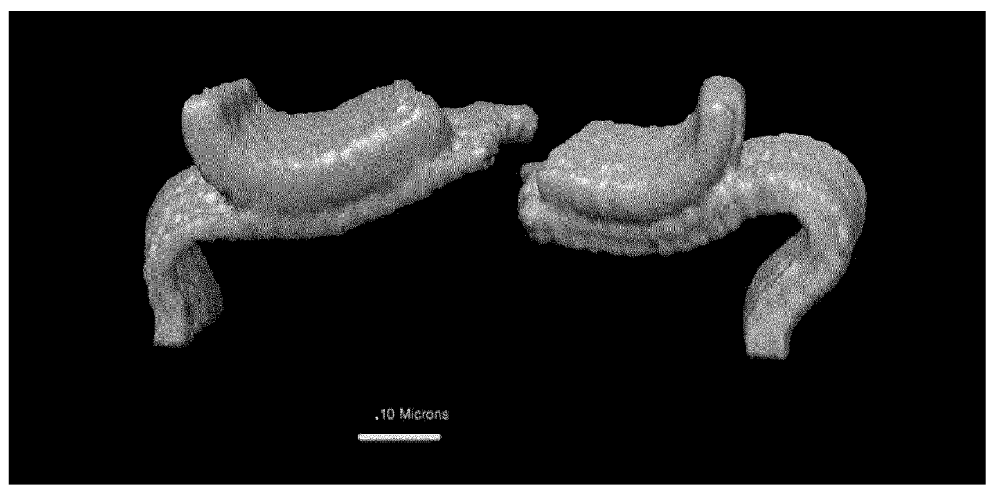

In some embodiments, the process according to the invention enables to create a plurality of conductive connections between two parallel surfaces. By selecting the shape of the three-dimensional actin structures to be formed, the process may enable to create both vertical and horizontal connections. To that respect, FIG. 8A illustrates that two adjacent chips may be connected together and to a parallel wafer by a connection having a "H-shape" which results from the interaction of two actin structure having T-shape.

Another object of the present invention is the conductive connection obtainable by the here-above process. The present invention also relates to a conductive network comprising horizontal and vertical connections obtainable by the metallization of the three-dimensional actin assembly as previously described.

A further object of the invention is an assembly comprising two surfaces, the said two surfaces being connected by conductive connections obtained by the process according to the present invention. In preferred embodiments, the said assembly is an electronic device and the said two surfaces are selected from silicon wafers or chips.

Further applications of the invention may be found in nano-material or in microfluidic technology.

The three-dimensional actin structure or assembly according to the invention may be used as sacrificial templates for creating micro-channels or micro-reactors in microfluidic systems or for creating hybrid materials. For example, three-dimensional structures may be prepared according to the invention within an appropriate reaction chamber. Once the said three-dimensional actin structures are obtained, the space surrounding the said structures may be filled with a liquid or viscous material such as a curable gel, polymer or wax. The said material solidifies and the actin structures are then removed (for example by chemical hydrolysis or depolymerization of actin), which leads to the creation of empty spaces having the shape of the initial actin structures within the cured material. For microfluidic applications, the said empty spaces may be used as micro-channels or micro-reaction chambers. The said empty spaces may be also filled with another material so as to provide composite or hybrid materials.

The three-dimensional actin structure according to the invention may also be used in microfluidic systems for immobilizing chemical entities such as chemical reagents, catalysts, ligands and the like. For example, several actin three-dimensional structures may be created within a microfluidic channel or a microfluidic reactor so as to form pylons, which are then functionalized with an appropriate chemical entity. Such a protocol enables to improve the interactions between the chemical reagents and the solution or gas that will flow inside the microfluidic channel. Indeed, such systems increase the contact surface between the chemical entity and the solution or the gas and may improve the activity of the immobilized entity.

Such systems can be used as a stationary phase for separating or detecting specific compounds present within a solution or a gas. In such a case, the immobilized chemical entity may be a ligand. These systems may also be used to improve the chemical reactivity of the entity within a reaction medium: in such a case, the entity may be a catalyst or a reagent.

The present invention is further illustrated, without being limited to, by the above examples.

EXAMPLES

The experiences were conducted with Arp2/3 from Bovine *thymus* or brain and with recombinant Mouse Capping protein αβ.

Example 1

"Plug and Receptacle" 3D Connections (See FIGS. 3A and 3B)

Two clean glass coverslips were made resistant to protein binding by a PLL-PEG treatment. The clean coverslips were first oxidized through oxygen plasma (FEMTO, Diener Electronics, France) 60 s at 30 W. The negatively charged coverslips were then incubated for 30 minutes with a 0.1 mg/mL PLL-PEG (CYTOO, France) diluted in 10 mM HEPES (pH 7.4). The positively charged PLL_PEG molecules were bound to the coverslips through electrostatic interactions creating a protein-repelling layer at their surfaces. After the incubation process, the two glass coverslips were washed with a 1×KMEI buffer to remove the unbound PLL-PEG that is in excess.

The 1×KMEI buffer is composed of 500 mM KCl, 10 mM $MgCl_2$, 10 mM EGTA and 100 mM imidazole at pH 7 diluted ten times in a G-Actin buffer (2 mM Tris-Cl, 0.2 mM ATP, 0.5 mM DTT, 0.1 mM $CaCl_2$ and 1 mM Na azide).

The two glass coverslips were then assembled together with one over the other thanks to two double face scotch pieces that have a thickness of 30 microns (Nitto, Japan). It enables to create a 30 μm per 10×15 mm reaction chamber. The inner surfaces of the reaction chamber were further washed with 100 μL of 1×KMEI buffer.

The both face of the reaction chamber were then patterned by a laser based patterning method. Laser patterning was performed using of a Laser illuminator iLasPulse (ROPER SCIENTIFIC, France) set up on an inverted microscope (TE2000-E, Nikon, France). The dual axis galvanometer based optical scanner iLasPulse focalized the Laser beam on the sample on the whole field of view of the camera. The laser used was a passively Q-switched laser (STV-E, TeamPhotonics, France) that produced 300 picoseconds pulses at 355 nm (Energy/Pulse 1.2 μJ). Laser displacement, exposure time and repetition rate were controlled using Metamorph® software (Universal Imaging Corporation). The objective used was a 100× CFI S Fluor oil objective (MRH02900, Nikon, France). The zone to pattern was filled with spot every 500 nm. Each spot was exposed for 5 ms at a repetition rate of 2000 Hz and an average energy per pulse of 400 nJ.

To self-assemble 3D connexions following a "plug and receptacle" manner we created on one of the reaction chamber face disk-shaped patterns with a diameter of 5 to 7.5 μm. On the other face we created ring-shaped patterns with an intern diameter of 10 to 15 μm and with an outline thickness of 4 μm. Each pattern on a face was aligned with its complementary pattern present on the other face.

During the patterning process the reaction chamber was filled with a solution containing the nucleating agent pWA (2 μM of pWA diluted in a 1×KMEI buffer). The nucleating agents bound then to the pattern while the said pattern was shaped by the laser irradiation. Once all the patterns were done, we washed the pWA solution by flowing 200 to 400 μL of 1×KMEI buffer within the reaction chamber. The patterned reaction chamber was then kept at 4° C. filled with 1×KMEI buffer until we used it again.

The polymerization solution comprised of 3 μM G-actin, 9 μM profilin, 25 nM Arp2/3 complex, 40 nM Capping Protein αβ in Xb buffer (10 mM Hepes pH 7.5, 0.1M KCl, 1 mM MgCl2, 0.1 mM $CaCl_2$ and 1 mM ATP), supplemented with 1% BSA, 0.5% Methylcellulose, 3 mM DTT, 0.13 mM DABCO and 1.8 mM ATP. The G-actin monomer were first mixed with the BSA and profilin protein for 3 minutes to create the complex G-actin—profilin. The final solution was then achieved and used to fill the reaction chamber composed of the two patterned surfaces. The reaction chamber was finally hermetically closed to prevent any flux or evaporation within the reaction chamber. In order to be able to image the structures, G-actin monomer were labelled with Alexa-488 or Alexa-568 fluorophores. In that case a ratio of 1:9 of labelled G-actin over unlabeled G-actin was used.

The polymerization of the structures began immediately after the filling of the reaction chamber with the polymerization solution and run on several hours. However, the structure did not elongate significantly after 1 hour. The interactions between the full structures on one face and the empty one on the other led to the creation of 3D connexions between the two surfaces of the "plug and receptacle" type. The obtained actin structures had a height of around 20 μm. No deformation of the actin substructures was observed after interaction.

Example 2

3D Column-Type Structures (FIG. 4)

Two clean glass coverslips were made resistant to protein binding by a PLL-PEG treatment. The clean coverslips were first oxidized through oxygen plasma (FEMTO, Diener Electronics, France) 60 s at 30 W. The negatively charged coverslips were then incubated for 30 minutes with a 0.1 mg/mL PLL-PEG (CYTOO, France) diluted in 10 mM HEPES (pH 7.4). The positively charged PLL_PEG molecules were bound to the coverslips through electrostatic interactions creating a protein-repelling layer at their surfaces. After the incubation process, the two glass coverslips were washed with a 1×KMEI buffer to remove the unbound PLL-PEG that is in excess. The 1×KMEI buffer was composed of 500 mM KCl, 10 mM MgCl2, 10 mM EGTA and 100 mM imidazole at pH 7 diluted ten times in a G-Actin buffer (2 mM Tris-Cl, 0.2 mM ATP, 0.5 mM DTT, 0.1 mM CaCl$_2$ and 1 mM Na azide).

The two glass coverslips were then assembled together with one over the other thanks to two double face scotch pieces having a thickness of 30 microns (Nitto, Japan). It enabled to create a 30 μm per 10×15 mm reaction chamber, which both faces anti-adhesives. We flowed 100 μL of 1×KMEI buffer through the reaction chamber to finish to wash the two surfaces.

The both face of the reaction chamber were then patterned thanks to a laser based patterning method. Laser patterning was performed using of a Laser illuminator iLasPulse (ROPER SCIENTIFIC, France) set up on an inverted microscope (TE2000-E, Nikon, France).

The dual axis galvanometer based optical scanner iLasPulse focalize the Laser beam on the sample on the whole field of view of the camera. The laser used was a passively Q-switched laser (STV-E, TeamPhotonics, France) that produced 300 picoseconds pulses at 355 nm (Energy/Pulse 1.2 μJ). Laser displacement, exposure time and repetition rate were controlled using Metamorph® software (Universal Imaging Corporation). The objective used was a 100× CFI S Fluor oil objective (MRH02900, Nikon, France). The zone to pattern was filled with spot every 500 nm. Each spot was exposed for 5 ms at a repetition rate of 2000 Hz and an average energy per pulse of 400 nJ.

To self-assemble 3D direct connexions, we created on the both faces of the reaction chamber disk-shaped patterns with a diameter of 5 to 10 μm. The patterns were vertically aligned two by two within the reaction chamber. During the patterning process the reaction chamber was filled with a solution containing the activator agent pWA (2 μM of pWA diluted in a 1×KMEI buffer). The activator agents bound then to the pattern while they were realized by the laser irradiation. Once all the patterns were done, we washed the pWA solution by flowing 200 to 400 μL of 1×KMEI buffer within the reaction chamber. The patterned reaction chamber was then kept at 4° C. filled with 1×KMEI buffer until we used it again.

The polymerization mix was composed of 3 μM G-actin, 9 μM profilin, 25 nM Arp2/3 complex, 40 nM Capping Protein αβ and 100 nM α-actinin in Xb buffer (10 mM Hepes pH 7.5, 0.1M KCl, 1 mM MgCl$_2$, 0.1 mM CaCl$_2$ and 1 mM ATP), supplemented with 1% BSA, 0.5% Methylcellulose, 3 mM DTT, 0.13 mM DABCO and 1.8 mM ATP. The G-actin monomer were first mixed with the BSA and profilin protein for 3 minutes to create the complex G-actin—profilin which prevented unwanted polymerization in solution and help the polymerization of the structure. The final mix of all the protein was then achieved and used to fill the reaction chamber composed of the two patterned surfaces. The reaction chamber was finally hermitically closed to prevent any flux or evaporation within the reaction chamber. In order to be able to image the structures created we had used G-actin monomer that were labelled with Alexa-488 or Alexa-568 fluorophores. In that case a ratio of 1:9 of labelled G-actin over black G-actin was used.

The polymerization of the structures began immediately after the reaction chamber filling with the polymerization mix and could run on several hours. However, the structure didn't elongate significantly after 1 hours and automatically stopped once the connexions are created due to the presence of cross-linker agents (α-actinin). This method enabled thus to create 3D direct connexions between the two faces of the reaction chamber. It also presents the advantage to automatically stop when the connexions are created which release the constraints on the structures length control. Moreover, the connexions created are resistant to the flow of 200 μL of 1× buffer within the reaction chamber.

Example 3

Building Blocks Having T-Shape Structure

Two clean glass coverslips were made resistant to protein binding by a PLL-PEG treatment. The clean coverslips were first oxidized through oxygen plasma (FEMTO, Diener Electronics, France) 60 s at 30 W. The negatively charged coverslips were then incubated for 30 minutes with a 0.1 mg/mL PLL-PEG (CYTOO, France) diluted in 10 mM HEPES (pH 7.4).

The positively charged PLL_PEG molecules were bound to the coverslips through electrostatic interactions creating a protein-repelling layer at their surfaces. After the incubation process, the two glass coverslips were washed with a 1×KMEI buffer to remove the unbound PLL-PEG that is in excess. The 1×KMEI buffer was composed of 500 mM KCl, 10 mM MgCl$_2$, 10 mM EGTA and 100 mM imidazole at pH 7 diluted ten times in a G-Actin buffer (2 mM Tris-Cl, 0.2 mM ATP, 0.5 mM DTT, 0.1 mM CaCl$_2$ and 1 mM Na azide).

The two glass coverslips were then assembled together with one over the other thanks to two double face scotch pieces that have a thickness of 30 microns (Nitto, Japan). It enabled to create a 30 microns per 10×15 mm reaction chamber, which both faces anti-adhesives. We flow 100 μL of 1×KMEI buffer through the reaction chamber to finish to wash the two surfaces.

The both face of the reaction chamber were then patterned thanks to a laser based patterning method. Laser patterning was performed using of a Laser illuminator iLasPulse (ROPER SCIENTIFIC, France) set up on an inverted microscope (TE2000-E, Nikon, France). The dual axis galvanometer based optical scanner iLasPulse focalize the Laser beam on the sample on the whole field of view of the camera. The laser used was a passively Q-switched laser (STV-E, TeamPhotonics, France) that produces 300 picoseconds pulses at 355 nm (Energy/Pulse 1.2 μJ). Laser displacement, exposure time and repetition rate were controlled using Metamorph® software (Universal Imaging Corporation). The objective used was a 100× CFI S Fluor oil objective (MRH02900, Nikon, France). The zone to pattern was filled with spot every 500 nm. Each spot was exposed for 5 ms at a repetition rate of 2000 Hz and an average energy per pulse of 400 nJ.

To self-assemble 3D building blocks as previously described, we created on both faces of the reaction chamber quarter ring-shaped patterns with an inter diameter of 10 μm and 4 μm thick wall. The patterns were vertically aligned two by two within the reaction chamber. During the patterning process the reaction chamber is filled with a solution containing the activator agent pWA (2 μM of pWA diluted in a 1×KMEI buffer). The activator agents bound then to the pattern while they are realized by the laser irradiation. Once all the patterns were done, we washed the pWA solution by flowing 200 to 400 μL of 1×KMEI buffer within the reaction chamber. The patterned reaction chamber is then kept at 4° C. filled with 1×KMEI buffer until we used it again.

The polymerization mix is composed of 6 μM G-actin, 18 μM profilin, 25 nM Arp2/3 complex, 40 nM Capping Protein αβ in Xb buffer (10 mM Hepes pH 7.5, 0.1M KCl, 1 mM MgCl$_2$, 0.1 mM CaCl$_2$ and 1 mM ATP), supplemented with 1% BSA, 0.5% Methylcellulose, 3 mM DTT, 0.13 mM DABCO and 1.8 mM ATP. The G-actin monomer were first mixed with the BSA and profilin protein for 3 minutes to create the complex G-actin—profilin that will prevent unwanted polymerization in solution and help the polymerization of the structure. The final mix of all the protein was then achieved and used to fill the reaction chamber composed of the two patterned surfaces. The reaction chamber was finally hermitically closed to prevent any flux or evaporation within the reaction chamber. In order to be able to image the structures created we used G-actin monomers labelled with Alexa-488 or Alexa-568 fluorophore. In that case a ratio of 1:9 of labelled G-actin over black G-actin was used.

The polymerization of the structures began immediately after the reaction chamber filling with the polymerization mix and could run on several hours. However, the structure didn't elongate significantly after 1 hour. The patterns created lead to the self-assembly of structures composed of a vertical connexion between the two faces of the reaction chamber and a horizontal branch that elongate in the opposite direction of the pattern orientation. Such structure could be used as building block toward the fabrication of more complex networks composed of several of them.

Example 4

Metallization of Actin Structure

Once the 3D actin structures within the reaction chamber were obtained, the structures were incubated with a Glutaraldehyde solution. 50 μL of a solution of 1% Glutaraldehyde diluted in a 2 mM Hepes buffer at pH 7.4 containing 0.1 mM KCl 1 mM $MgCl_2$ and 0.1 mM CaCl2 was flowed through the reaction chamber wherein the 3D actin structures were and was incubated 10 minutes. After the incubation time, the reaction chamber was washed with 100 μL of the 1×KMEI buffer to remove all the glutaraldehyde solution.

The reaction chamber was then filled with a solution containing metallic ions. Metallic ions were reduced by the glutaraldehyde moieties fixed on the actin structures to create metallic clusters on the 3D structures. 50 μL of a solution of 0.3 mM $HAuCl_4$ in a 2 mM Hepes buffer at pH 7.4 containing 0.1 mM KCl 1 mM $MgCl_2$ and 0.1 mM $CaCl_2$ was flowed through the reaction chamber and was incubated overnight (around 16 h) at 4° C. in contact with the 3D actin structures. The next day the reaction chamber was washed with 100 μL of the 1×KMEI Buffer to remove the $HAuCl_4$ solution. Actin structures coated with metallic Au cluster all along their lengths were obtained.

The metallic clusters were then used to catalyze an electro-less metallization process in order to completely coat the actin structures with a metallic layer. The reaction chamber was filled with 50 μL of a commercial electro-less metallization solution, the solution GoldEnhance® from Nanoprobes. The GoldEnhance® solution was prepared following the Nanoprobes instructions. Equal volumes of the solution A and B were first mixed together and authorized to rest 5 minutes. Equal volumes of the solution C and D were then added to the first mix and directly flowed through the reaction chamber. The electro-less metallization solution was incubated 10 minutes in contact with the 3D actin structures. The electro-less metallization process was finally stopped by flowing 100 μL of the 1×KMEI buffer to remove all the electro-less metallization solution within the reaction chamber. The 3D actin structures were now entirely coated with a metallic layer, here a gold layer.

Once the 3D actin structures were metallized, the said structures were dried to fulfil the microelectronics constraints. For this aim, the solution within the reaction chamber was slowly replaced by a 100% Ethanol solution. The reaction chamber was first washed with a solution of 10% Ethanol within pure water, then with a solution of 20% Ethanol within pure water until to reach a 100% Ethanol solution. The reaction chamber was then dried at ambient air. Once all the ethanol was evaporated, the 3D actin structures coated with a metallic layer that form a 3D conductive backbone were obtained.

Example 5

Preparation of an Array of Three Dimensional Actine Structures of the Column Type Deep UV Micro-Patterning Coverslips were first spin-coated for 30 seconds (s) at 1000 rpm with adhesion promoter TI-Prime (MicroChemicals, Germany), backed for 5 min at 120° C. and then spin-coated with 1% polystryrene (SIGMA, France) in toluene (SIGMA, France) at 1000 rpm for 30 s. Polystyrene coated coverslips were oxidized with oxygen plasma treatment (FEMTO, Diener Electronics, France) for 30 s at 60 W before incubating with 0.1 mg/mL PLL-PEG (JenKem Technology, USA) in 10 mM HEPES pH=7.4 for 30 min. After drying, pegylated coverslips were exposed to deep UV (UVO cleaner, Jelight, USA) through a photomask (TOPPAN, France) for 5 min.

To graft the nucleation promoting factor pWA on the UV-exposed coverslips, they were mounted on a pegylated glass slide with calibrated spacers of 180 μm (LIMA, France) to define a reaction chamber. The reaction chamber was filled with a solution of pWA at 1 μM for 15 min and then rinsed with KMEI buffer (500 mM KCl, 10 mM $MgCl_2$, 10 mM EGTA and 100 mM imidazole at pH 7.8 diluted ten times in a buffer (2 mM Tris-Cl, 0.2 mM ATP, 0.5 mM DTT, 0.1 mM $CaCl_2$ and 1 mM Na azide). The reaction chamber was then stored at 4° C. before its use.

Actin Polymerization Solution

Protein mixtures were diluted in freshly X buffer (10 mM HEPES, pH 7.4, 0.1M KCl, 1 mM $MgCl_2$, 1 mM ATP, and 0.1 mM $CaCl_2$) supplemented with 1% BSA, 0.2% methylcellulose, 3 mM DTT, 0.13 mM DABCO, 1.8 mM ATP. Actin polymerization without capping protein was induced in a solution containing 3 μM actin monomers (10% labelled with alexa 568), 9 μM profilin, 2 μM Phalloidin, and 50 nM Arp2/3 complex (comparative). Actin polymerization with capping protein was induced in a solution containing between 1.5 μM and 4.5 μM actin monomers (10% labelled with alexa 568), three equivalents of profilin, 2 μM Phalloidin, 50 nM Arp2/3 complex and 60 nm capping protein (invention).

Results

Figure 11:
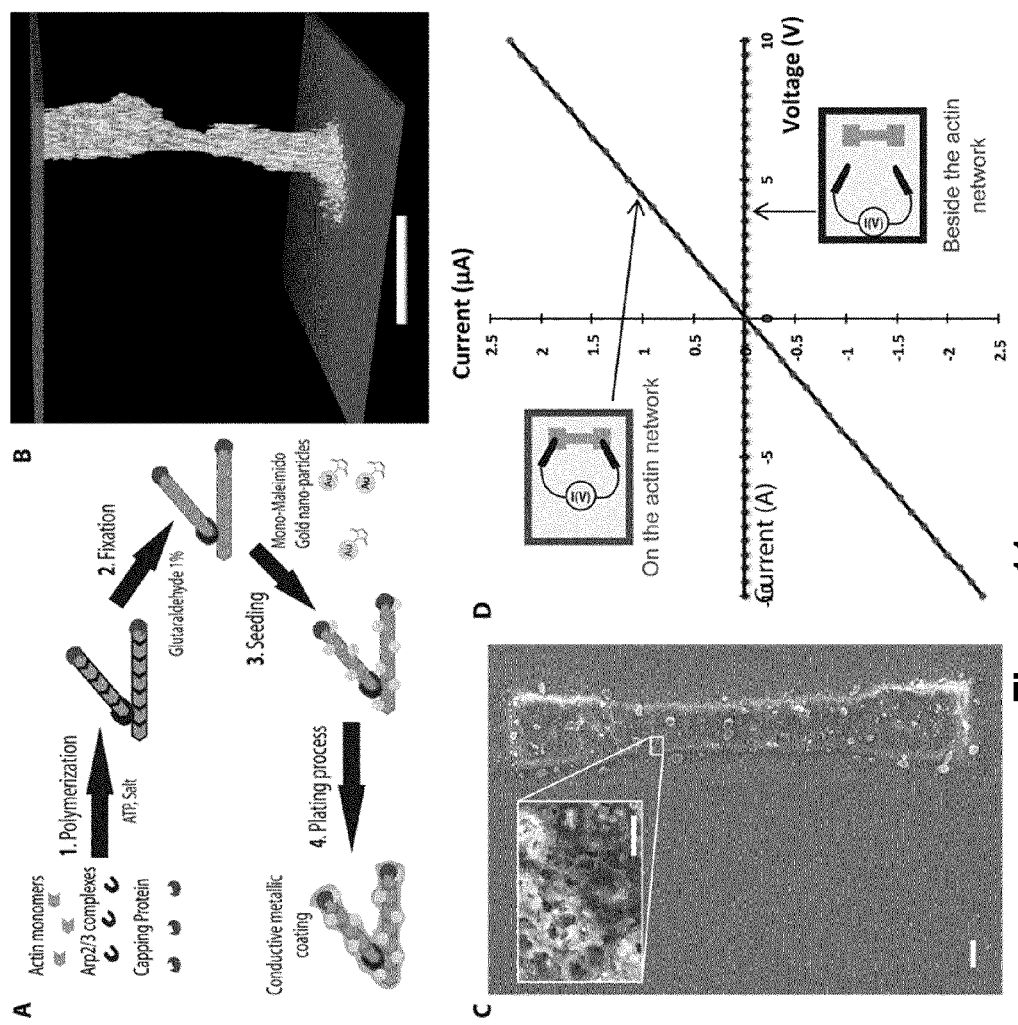
FIG. 11A shows the schematic representation of another metallization process based on the use of mono-maleimido gold nanoparticles (example 6).
FIG. 11B shows the 3D visualization of a 3D metallized actin structure. Reflection microscopy revealed the reflected light on metallic particles coated on the actin structure connecting the two opposing surfaces (glass slides).
FIG. 11C shows the scanning electron microscopy image of the metallized planar actin network that was used for conductivity measurements. The inset shows a magnification of interconnected gold aggregates.
FIG. 11D shows the electrical characterization of metallized planar actin networks. Current intensity was measured for various voltage tensions applied on the networks. Control measurements were performed in an area adjacent to the metallized planar actin network. Scale bars represent 10 µm in FIG. 11B and FIG. 11C and 1 µm in the inset.

FIGS. 11A and 11B further shows the crucial impact of capping protein on the final structure of three-dimensional actin network. The micropatterns coating with pWA enabled to control the localization of actin polymerization but in the absence of capping protein in the polymerization solution, actin filaments were randomly distributed all around the nucleation sites (FIG. 11A) to give flower-like structures. When capping protein was present in the polymerization solution, the Applicant obtained dense and reticulated actin networks from each torus-shaped micropattern. The actin networks had a regular tube-like shape (FIG. 11B) with a cross-section consistent with the dimension of the micropattern.

Figure 10:
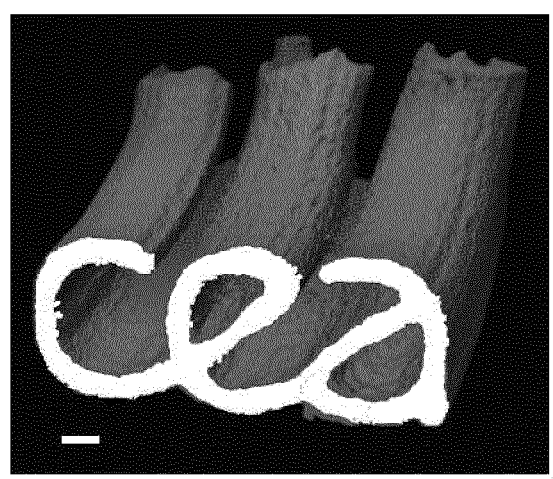
FIG. 10 shows the 3D visualization of a large actin network that polymerized out of a CEA-shaped micro-pattern. The structure was made of 3 µm wide vertical walls that are 36+/-3 µm high. Scale bar represents 5 µm.

As fully-illustrated herein, the method of the invention may be used to generate 3D structures of various sizes and shapes by modulating the micropattern dimensions and the quantity of actin monomers, Arp2/3 and capping protein. For example, micropatterned glass slides with arrays of 0.8 and 1.5 µm wide dots led to the growth of 2.4 and 3 µm high micropillars. On the other hand, much larger structures could be obtained by using higher concentration of actin monomers on larger micropatterned regions. For example, we generated an 18 µm wide and 36 µm high 3D version of the institute logo CEA (made of 3 µm wide walls) (see FIG. 10).

Example 6

Another Example of Metallization Process and Conductivity Characterization

Metallization Process

Actin structures were fixed 1 h after polymerization (see above Example 5), with a solution of glutaraldehyde at 1% diluted in KMEI buffer for 20 min and then rinsed with ultra pure water. This step was performed to rigidify the network and increase its resistance to the fluid flow and the biochemical conditions during metallization. The mechanical resistance of the actin structures was further improved by adding alpha-actinin, an actin filament cross-linking protein, in the polymerization solution. The actin structures were then incubated overnight at 4° C. with a solution of Mono-Maleimido Nanogold® particles (Nanoprobes, USA) diluted in 50 mM of NaPl buffer (pH 7.4). The electroless metallization process was then performed with a Golenhance® LM kit (Nanoprobes, USA). A first incubation step was done in Goldenhance® solution diluted 5 times in his buffer for 1 hour. After rinsing with ultrapure water, a second incubating step was performed with Goldenhance® solution diluted twice for 20 min. A final incubation step was then performed with non-diluted Goldenhance® solution for 7 min. The structures were then rinsed with ultrapure water and were allowed to dry at air.

The polymerization of actin structure and the metallization step are illustrated in FIG. 11A.

Conductivity Characterization

Conductivity characterization of 2D metallized actin networks was performed on a Cascade Microtech S300 probe station (Cascade Microteh, USA). The electrical measurements were done by using DCM-210 Presicion Positioner (Cascade Microtech, USA) to position two probes on each extremity of a 200 µm-long metallized actin network. The I-V curve measurements on and adjacent to the metallized actin networks were performed between −10 V and 10 V every 1 V using a 4156C Precision Semiconductor Parameter Analyzer (Agilent, USA).

Results

FIG. 11B shows the 3D reconstruction in reflection microscopy of the gold coating on one of the resulting metallized actin structures. The resulting structures were sufficiently strong to resist all fluid exchanges and the harsh chemical conditions during metallization. FIG. 11C provides the scanning electron image of one of said metallized structures, which reveals the presence of large aggregates corresponding to salt precipitates and smaller clusters corresponding to the gold-coated particles. The electrical properties of metallized dense actin networks were characterized using a 2-point measurement technique. A 100 µm-long metallized-actin meshwork assembled on a planar surface provided a sufficient access for the two electrodes. The electrical measurement method consisted in measuring the current through the electrodes in contact with the actin network. Although no current was measured when the electrodes were in contact with the surface next to the metallized actin meshwork, currents of a few micro-Amperes could be measured in the network in response to a few Volts (FIG. 11D). We observed linear I-V curves, evidence of an ohmic conduction, with resistance ranging from $5.10^8$ to $4.10^9 \Omega$ depending on the metallization batch and the structure measured. These results demonstrate that the metallized actin networks obtained by the method according to the invention were conductive.

The invention claimed is:

1. A method for preparing a three dimensional structure of actin, said method comprising the steps of:
   a) providing a polymerization solution comprising actin monomers, an Arp2/3 complex, a capping agent, ATP, a divalent cation and profilin wherein the molar ratio of Arp2/3 to capping agent ranges from 0.1 and 4.0;
   b) providing at least one surface having thereon at least one pattern, the said pattern being coated with a nucleating agent selected from the group consisting of members of the WASp family, members from SCAR/WAVE family, VCA domains thereof, peptides from VCA domains, functional homologs of SCAR/WAVE and WASp proteins and combinations thereof; and
   c) contacting the at least one surface of step (b) with the polymerization solution of step (a) so as to induce the polymerization of actin and obtain the said three-dimensional actin structure.

2. The method of claim 1, wherein:
   in step b), a first surface and a second surface are provided, wherein each surface has thereon a pattern coated with a nucleating agent and the said first and second surfaces are positioned so as that:
      the said surfaces are substantially parallel to each other and separated by a distance of at most 1 mm, and
      the pattern of the first surface and that of the second surface are face-to-face so that their centers are substantially aligned; and
   in step c), the two patterned surfaces of step b) are contacted with the polymerization solution of step a) so as to induce the polymerization of a tridimensional actin substructure from each said pattern, thereby the final three-dimensional actin structure results from the interaction of the two actin substructures which have grown face-to-face from said patterns.

3. The method of claim 1, wherein the polymerization solution of step a) has a molar ratio of actin monomers to the Arp2/3 complex ranging from 5 to 500.

4. The method of claim 1, wherein in the polymerization solution of step a), the molar ratio of actin monomers to the Arp2/3 complex ranges from 5 to 20.

5. The method of claim 1, wherein in the polymerization solution of step a), the molar ratio of actin monomers to the Arp2/3 complex ranges from 20 to 50.

6. The method of claim 1, wherein, in the polymerization solution of step a), the concentration of actin monomers ranges from 0.01 µM to 100 µM.

7. The method of claim 1, wherein the polymerization solution further comprises a cross-linking protein, the molar ratio of said cross-linking protein to Arp2/3 complex ranging from 0.1 to 5.

8. The method of claim 2, wherein the first surface and the second surface provided in step b) have thereon a plurality of patterns so that the center of each pattern on the first surface is substantially aligned with that of a pattern on the second surface.

9. The method of claim 2, wherein:
the pattern on the first surface has a shape complementary to that of the pattern on the second surface, or
the pattern on the first surface has the same shape as the pattern on the second surface.

10. The method of claim 1, wherein step c) is followed by one or several of the following steps:
a step of removing the polymerization solution once the three-dimensional actin structure has been obtained,
a step of incubating the three-dimensional actin structure obtained in step c) with a solution comprising a cross-linking protein,
a step of incubating the three-dimensional actin structure obtained in step c) with a solution comprising a chemical cross-linker, a chemical fixative agent and/or an agent able to inhibit actin depolymerization,
a step of chemically functionalizing the three-dimensional actin structure obtained in step c), and/or
a step of metallization of the three-dimensional actin structure obtained in step c).

11. A three dimensional actin structure obtainable by the method of claim 3.

12. A device comprising at least one planar surface which comprises thereon at least one actin three-dimensional structure obtained according to the method of claim 1.

13. The device of claim 12 which comprises two surfaces substantially parallel to each other wherein the said surfaces are connected to each other by said at least one three-dimensional actin structure.

14. A process for creating a conductive or a semi-conductive connection between two surfaces comprising the steps of:
i) preparing a three dimensional actin structure by the method of claim 1,
ii) coating the three-dimensional structure of actin obtained in step i) with a conductive or semi conductive layer, and
iii) optionally, removing the backbone of actin.

15. The process of claim 14, wherein step (ii) comprises submitting the three-dimensional actin structure obtained in step i) to a metallization process so as to coat the said three dimensional structure of actin with a conductive metallic layer.

16. An electronic device comprising two surfaces which are connected together by at least one conductive connection wherein said at least one conductive connection is obtained by the process of claim 14.

17. The electronic device of claim 16, wherein the two surfaces are selected from chips and silicon wafers.

* * * * *